US010273475B2

(12) United States Patent
Irminger-Finger et al.

(10) Patent No.: US 10,273,475 B2
(45) Date of Patent: Apr. 30, 2019

(54) REGULATION OF BARD1 EXPRESSION BY NON-CODING RNA

(71) Applicants: Irmgard Irminger-Finger, Genêve (CH); Maxim Pilyugin, Onex (CH)

(72) Inventors: Irmgard Irminger-Finger, Genêve (CH); Maxim Pilyugin, Onex (CH)

(73) Assignee: BARD1 LIFE SCIENCES LIMITED, Perth Wa (AU)

( * ) Notice: Subject to any disclaimer, the term of this patent is extended or adjusted under 35 U.S.C. 154(b) by 0 days.

(21) Appl. No.: 14/797,148

(22) Filed: Jul. 12, 2015

(65) Prior Publication Data

US 2016/0319276 A1 Nov. 3, 2016

(30) Foreign Application Priority Data

Jul. 12, 2014 (EP) .................................... 14002398

(51) Int. Cl.

*C12N 15/11* (2006.01)
*C12N 15/113* (2010.01)
*G01N 33/50* (2006.01)
*C12Q 1/6886* (2018.01)

(52) U.S. Cl.

CPC ........ *C12N 15/113* (2013.01); *C12N 15/1135* (2013.01); *C12Q 1/6886* (2013.01); *G01N 33/5011* (2013.01); *C12N 2310/113* (2013.01); *C12N 2310/14* (2013.01); *C12N 2310/141* (2013.01); *C12N 2330/10* (2013.01); *C12Q 2600/158* (2013.01); *C12Q 2600/178* (2013.01)

(58) Field of Classification Search

None

See application file for complete search history.

(56) References Cited

PUBLICATIONS

Jackson et al., Expression profiling reveals off-target gene regulation by RNAi, 2003, Nature Biotechnology, vol. 21, pp. 635-637.*

Hanning et al., Lack of correlation between predicted and actual off-target effects of short-interfering RNAs targeting the human papillomavirus type 16 E7 oncogene, 2013, British Journal of Cancer, vol. 108, pp. 450-460.*

Watanabe et al., Endogenous siRNAs from naturally formed dsRNAs regulate transcripts in mouse oocytes, 2008, Nature, vol. 453, pp. 539-543.*

Predicted: *Homo sapiens* lysine demethylase 5D (KDM5D), transcript variant X8, misc_RNA, GenBank No. XR_430568.3, accessed and retrieved from www.ncbi.nlm.gov on Apr. 19, 2017.*

*Homo sapiens* frizzled class receptor 3 (FZD3), transcript variant 1, mRNA, GenBank No. NM_017412.3, accessed and retrieved from www.ncbi.nlm.gov on Apr. 19, 2017.*

*Homo sapiens* gamma-aminobutyric acid type A receptor alpha4 subunit (GABRA4), trasncript variant 1, mRNA, GenBank No. NM_000809.3, accessed and retrieved from www.ncbi.nlm.gov on Apr. 19, 2017.*

NCBI Blast Global Alignment using AK310759.1 (922 letters), accessed and retreived from blast.ncbi.nlm.nih.gov on May 24, 2018.*

Pilyugin, M., et al., "Long non-coding RNA and microRNAs might act in regulating the expression of BARD1 mRNAs." The International Journal of Biochemistry & Cell Biology 54 (2014); pp. 356-367; available online Jul. 5, 2014.

Ryser S., et al., "Distinct Roles of BARD1 isoforms in Mitosis: Full-Length BARD1 Mediates Aurora B Degradation, Cancer-Associated BARD1β Scaffolds Aurora B and BRCA2." American Association for Cancer Research 2009; 69: (3); Feb. 1, 2009; Published online first Jan. 27, 2009; pp. 1125-1134.

Doan, C., et al., Simultaneous silencing of VEGF and KSP by siRNA cocktail inhibits proliferation and induces apoptosis of hepatocellular carcinoma Hep3β cells, Biological Research, 2014, 47:70; pp. 1-15.

Zhang, Y.Q., et al., "BARD1: an independent predictor of survival in non-small cell lung cancer." International Journal of Cancer. Jul. 1, 2012; 131(1): pp. 83-94. Epub Dec. 21, 2011.

* cited by examiner

*Primary Examiner* — Dana H Shin

(74) *Attorney, Agent, or Firm* — Rothwell, Figg, Ernst & Manbeck, P.C.

(57) ABSTRACT

The present invention relates to a long non-coding BARD1 RNA molecule named BARD1 9'L. The present invention also relates to siRNAs for therapeutic use, for example, the regulation of BARD1 expression by non-coding RNA. The present invention further relates to methods for the detection of BARD1 9'L. Finally, the present invention relates to promoters driving the expression of BARD1 9'L.

3 Claims, 7 Drawing Sheets

Specification includes a Sequence Listing.

NM_000465.2
NM_000465.3
ATG (1)
Genomic poly-(A)
(2458)
rs7585356
(3427)
mRNA poly-(A)
(5364)
pATG_F
p8_F
p10_F
p11_R1
p11_R2
p11_R3
p11_R4
p11_R5
p11_R6

FL BARD1
α
κ
β
π
γ
φ
δ
ε
η

RT:
p11_R2
p11_R3
2.5
2.0
1.5
1.0
0.8
0.6
0.4
FL
β
π
γ
φ
δ
ε
η

RT:
p11_R5
p11_R6
p11_R2
Oligo-(dT)
BARD1 FL
p8_F - p11_R4
BARD1β
BARD1γ
BARD1δ
BARD1 9'L
p6_F - p11_R1

FIG. 2C

```
hsa-miR-513c
     uauuUGCUGUGGAGGAACUCUu     SEQ ID NO: 82
          |  ||:|||  |||||||
UGAGUGGGCAGGAUACC-ACUUGAGAGUGGCCAGAUGUGGG 3447 SEQ ID NO: 83

hsa-miR-514b-5p
    uacuaacggAGGGAGAACUCUu  SEQ ID NO: 84
               |  ||  |||||||
UGAGUGGGCAGGAUACCACUUGAGAGUGGCCAGAUGUGGG 3447 SEQ ID NO: 85

hsa-miR-588
        caagauUGGGUAA----CACCGGUu SEQ ID NO: 86
                  |||  ||    |||||||
UGAGUGGGCAGGAUACCACUUGAGAGUGGCCAGAUGUGGG 3447 SEQ ID NO: 87

hsa-miR-668
caUCACCCG------GCUCGG--CUCACUGu SEQ ID NO: 88
  |||||||       | | |:  |||||:
UGAGUGGGCAGGAUACCACCUGAGAGUGGCCAGAUGUGGG 3447 SEQ ID NO: 89
```

FIG. 2D

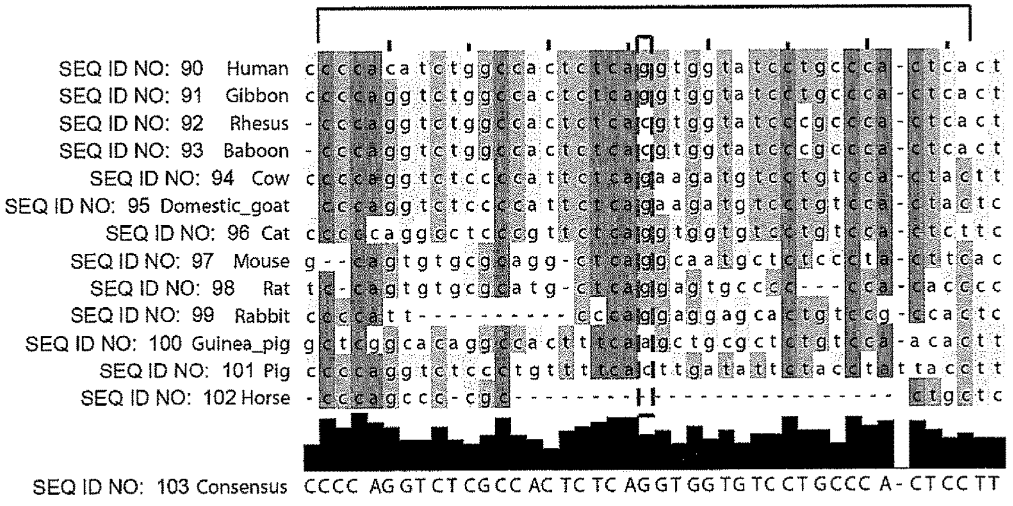

9
9'
10
11
BARD1 9'L
BARD1 9'S
p9'_F1
p9'_F2
p11_R1
p11_R3

SEQ ID NO: 104 AAA ATG AGC AGT ATA GAT GGG GTA AAA GCA TGT CTA CGA
SEQ ID NO: 105 M S S I D G V K A C L R

MW
BARD1 9'L
BARD1 9'S
1.5
1.0
0.8

MCF7
A549
DU145
LNCap
BARD1 9'L
BARD1 9'S
GAPDH
1.0
0.8
0.6
0.4

SEQ ID NO: 103
ERE
Cluster 1
Cluster 2
9'-10
11
9
H3K27 acetylation
DNAse I hypersensitivity
Transcription factors

SEQUENCE LISTING

```
<160> NUMBER OF SEQ ID NOS: 105

<210> SEQ ID NO 1
<211> LENGTH: 4328
<212> TYPE: RNA
<213> ORGANISM: Homo sapiens

<400> SEQUENCE: 1

guccugggaa ucccaagggu uccuuucauu ucuagagccu agcgagacaa uugguacugg      60

cugccagcca guggcccuac uuagggauuc cccacccagg ugccaagcag uggaaugacu     120

cuaaacagug ccaggcugag cugucucuau ugcuuuugcu uuuuaaccug aagcugugaa     180

cagacuuacu caagccauca aaagaaugcu uuuuuuuuuu ccugcaaagc ccaaucaaau     240

caucucuaga cuagcaaccu caguugugua ccugucacau gccaaaccua ucccaagcuc     300
```

-continued

```
ugcuuguuua uuuuaggaag cgcuguugaa ccccuguugu guggcuagcu gagcuuggug    360
cuguagacua aagcacauuc cuucauguca aaucacuuac aguuuaacag acgauuagac    420
auauaacugu caaaaugagc aguauagaug guaagugcuc aguuuagguu auugugucau    480
ggacuuuuua uucaccuuaa uuuugggua a uugcuaugag uggaaaugua gacuuuuauu    540
uuugucuuug aaauaguauc cuggcuuagg uuuuucagaa aggagauuaa aauuacaguu    600
aguguucagu acuaacuuau ggcuuaaucc uccaaagaaa gaguuuuuua aaauauuuuc    660
uuuauauggg aaaaccaguu guauuacauu uuguuuuggc auaaguaaga uuucuguuug    720
cauuuuagaa uaauacuuaa aaacugccau gaagaagaaa aaccacuuag guaaauugcu    780
ugauuuuaau gagagagaua uagugcucac uugauacuua guuugcuuua auucuugugu    840
uuuugucagg gguaaaagca ugucuacgaa gaaaaguaug ugaacaggaa gaaaaguaug    900
aaauuccuga agguccacgc agaagcaggc ucaacagaga acagcuguug ccaaagcugu    960
uugauggaug cuacuucuau uuguggggaa ccuucaaaca ccauccaaag gacaaccuua   1020
uuaagcucgu cacugcaggu gggggccaga uccucaguag aaagcccaag ccagacagug   1080
acgugacuca gaccaucaau acagucgcau accaugcgag acccgauucu gaucagcgcu   1140
ucugcacaca guauaucauc uaugaagauu uguguaauua ucacccagag aggguucggc   1200
agggcaaagu cuggaaggcu ccuucgagcu gguuuauaga cugugugaug uccuuugagu   1260
ugcuuccucu ugacagcuga auauuauacc agaugaacau uucaaauuga auuugcacgg   1320
uuugugagag cccagucauu guacuguuuu uaauguucac auuuuuacaa auagguagag   1380
ucauucauau uugucuuuga aucaaaaaaa aaaaaaaaag ucuaaugcca gauuaggaau   1440
ucauguugug uuuaccauuu agaagcuggg auugcuuuua aagguuuuuc uuuuuaaaau   1500
uggcauguuu uugauuuauc augucuuucu auucagauua uuggguauca aagauuaaug   1560
aggacaccag aaucuugguu aaauagacaa gugguaucau uacuguuuga gucuuuuaau   1620
auucuccaua ccugccacca gugaaaaaac uugccuuuuu uuuuuuuuuu uuuuuaguaa   1680
acagaauauu aucaaacaau uuauuuuggc uuuauugaaa aaagaguauu uggucuaaau   1740
gugccaccau agguguuaaa uucuccuauc ugcaauuguc uuuauccuau auuguguuca   1800
uuucuuuucu uaauaauuua cuuuguugug uguuucuaca cuuucauccc uguuuuuuau   1860
cuuguauauc aucaggaaau ugugauuuaa ucauuaacau ugguuuuuuu gugugugugg   1920
uaaaaaucaa cacuaggcuc augguacaua uuuuuauucu guacauuugc uuguaacuau   1980
caauuuguaa cucuguuuau cuacuacaug uguauauaua cuuagagcau uuucucuaac   2040
acauuuuaau guuaguauuu uuuaaaaggu cugaccaguc uagcaaauug ucaguccaac   2100
gucauuacuu uaaauuaaga agcagucuuc uucugguaaa ccuuguuggu auuuguaaaa   2160
uaauuuugaa ggucuuaauu ucuuccuuug uaaaaggaaa agguuuuuuu uaaaguuuuu   2220
agguuggcau ggaggcagaa guuggugauu acuugauuua caacagauuu uuuccagauc   2280
auacaaaagg ccauacagua aguauagaag uagguauggg gagggcuuac uaauaucaaa   2340
uaggcaaggc cuuagugagu gggcaggaua ccaccugaga guggccagau guggggaggu   2400
uacucugcuc ugggugcucu cauucaugaa ucgacaagga uacauuagau uauuuugaaa   2460
cauuuuuuua agaagcagaa uucuuuaaua auuccuuccu agacauugaa uauacuuaua   2520
aaauuaaaga cuuggggaag gagacacuga gagacuugcc aguuugguuc cucaugaaca   2580
aaagaggaca guuugauaac uaccagaaua gaauaucccu aguuuuaaaa uagugagaau   2640
```

-continued cucugaaguu caucaacauc uuaagaugca cuuacuugaa aguuugagau ucuguuuauc 2700
auuugaaaac acauuuugcu uuaauucuuu cuuugacaug uuguuuuuuc auaucaagaa 2760
auauaugaac aaaauaauaa ccuuuugacc cugaccuugc ugggugaauu agcucugaaa 2820
cacucucuac aaccaguaau gcauuugucc cacauuucau ucugauagaa aaugaacacc 2880
auagcaccaa acaaaaaucc gaggcguuag auaaaugucug gauuaaauaa uuuaagacuc 2940
ucuaggauuu ugguugucau uuuuuauuua uaacagacuu uaagucacuu ucuguugccu 3000
cauaggucac auuuuagaca gguuuguguc uguuccuugc aucugaauuc cugauuguaa 3060
agacaccuau gaggucucuu aguuuuuguc auucauuuuc uugguuuauc accccucccu 3120
ucuuuuuguu guuuuucccu gacuguuaag caguuucauc uuugcuuuug uuaaauauuu 3180
gacagcaguu aguuuguguu aagcucuuga aacuugugau uguacuuucu guguagauau 3240
acauguaauu auuuuuuauu uuucaaucau agauucaagc uuccuucuuu uuuaccacaa 3300
aucauuaaag uuauuuugugu uuccauauac cugugucuug uauaaaauug gcuuauucug 3360
ugcuguugaa ugaggcucaa caugacuugg ugaggaaguc uauuaacuaa caaaagcuua 3420
ucuuuuuuaa cauaaaugcuu uuuaauuaau uuugaauaaa aauauuucua aaguguacua 3480
gauacuuuau uaccuuagau uauuccgaau acaguauaac uuugauaguu uggaauaguc 3540
auuaagaaac aauuacacac ugauugcuuu gugucucuaa aagugagagg cugguagcuu 3600
uuccacauuc ucauggcuau uuucuaguuc uacuugaauu uauaacuguu ucccuuuuuc 3660
cuugacagcu gccacuuugu agcuauuuuu cugucucugc uaauacuuua ccauaucuau 3720
cucaauuguu uuuucuuuug acuugcugaa aaauagaaac cagaugggaa guauauuagc 3780
auuaugauug aaauaagggu aaaugagcaa ugugugaagg uuuucacuga cuucaccuaa 3840
aagauaguuu agcuacuuga auuuuaguaa auagaauuuu uccuuuauuu caucgguccc 3900
cccaccuuuu uuuuuuuuug caccugccuu guaaauuuaa uaguuaagug accucugccu 3960
agaggaugau auuuggggag guuugauguu uccugugga auaagacgau ucacagguga 4020
gaguggggcc acauuagcug uuauuguuuc caugggucag uguggaaaau gcauuaauca 4080
uauucuaaac guucaugggc cucauuacag ucacaauugu cuauucuguu uccuacccug 4140
aacacauuaa aaugguagga acuaaugcuu gucuuauuua auuacuaaaa gccaccauuu 4200
ucuuugauag auugagcuac agauuguaaa cuucauguau uucuuuauaa gucaacccuu 4260
uucaaagaua cgcacaucaa acugaaugaa uaaauaaaua uugagaaguu gaaaaaaaaa 4320
aaaaaaaa 4328

<210> SEQ ID NO 2
<211> LENGTH: 849
<212> TYPE: RNA
<213> ORGANISM: Homo sapiens

<400> SEQUENCE: 2
guccugggaa ucccaagggu uccuuucauu ucuagagccu agcgagacaa uugguacugg 60
cugccagcca guggcccuac uuagggauuc cccacccagg ugccaagcag uggaaugacu 120
cuaaacagug ccaggcugag cugucucuau ugcuuuugcu uuuuaaccug aagcugugaa 180
cagacuuacu caagccauca aaagaaugcu uuuuuuuuuu ccugcaaagc ccaaucaaau 240
caucucuaga cuagcaaccu caguugugua ccugucacau gccaaaccua ucccaagcuc 300
ugcuuguuua uuuuaggaag cgcuguugaa ccccuguugu guggcuagcu gagcuuggug 360
cuguagacua aagcacauuc cuucauguca aaucacuuac aguuuaacag acgauuagac 420

-continued

```
auauaacugu caaaaugagc aguauagaug guaagugcuc aguuuagguu auugugucau    480

ggacuuuuua uucaccuuaa uuuuggguaa uugcuaugag uggaaaugua gacuuuuauu    540

uuugucuuug aaauaguauc cuggcuuagg uuuuucagaa aggagauuaa aauuacaguu    600

aguguucagu acuaacuuau ggcuuaaucc uccaaagaaa gaguuuuuua aaauauuuuc    660

uuuauauggg aaaaccaguu guauuacauu uuguuuuggc auaaguaaga uuucuguuug    720

cauuuuagaa uaauacuuaa aaacugccau gaagaagaaa aaccacuuag guaaauugcu    780

ugauuuuaau gagagagaua uagugcucac uugauacuua guuugcuuua auucuugugu    840

uuuugucag                                                            849
```

<210> SEQ ID NO 3
<211> LENGTH: 947
<212> TYPE: RNA
<213> ORGANISM: Homo sapiens

<400> SEQUENCE: 3

```
guccugggaa ucccaagggu uccuuucauu ucuagagccu agcgagacaa uugguacugg     60

cugccagcca guggcccuac uuagggauuc cccacccagg ugccaagcag uggaaugacu    120

cuaaacagug ccaggcugag cugucucuau ugcuuuugcu uuuuaaccug aagcugugaa    180

cagacuuacu caagccauca aaagaaugcu uuuuuuuuuu ccugcaaagc ccaaucaaau    240

caucucuaga cuagcaaccu caguugugua ccugucacau gccaaaccua ucccaagcuc    300

ugcuuguuua uuuuaggaag cgcuguugaa ccccuguugu guggcuagcu gagcuuggug    360

cuguagacua aagcacauuc cuucauguca aaucacuuac aguuuaacag acgauuagac    420

auauaacugu caaaaugagc aguauagaug guaagugcuc aguuuagguu auugugucau    480

ggacuuuuua uucaccuuaa uuuuggguaa uugcuaugag uggaaaugua gacuuuuauu    540

uuugucuuug aaauaguauc cuggcuuagg uuuuucagaa aggagauuaa aauuacaguu    600

aguguucagu acuaacuuau ggcuuaaucc uccaaagaaa gaguuuuuua aaauauuuuc    660

uuuauauggg aaaaccaguu guauuacauu uuguuuuggc auaaguaaga uuucuguuug    720

cauuuuagaa uaauacuuaa aaacugccau gaagaagaaa aaccacuuag guaaauugcu    780

ugauuuuaau gagagagaua uagugcucac uugauacuua guuugcuuua auucuugugu    840

uuuugucagg gguaaaagca ugucuacgaa gaaaaguaug ugaacaggaa gaaaaguaug    900

aaauuccuga agguccacgc agaagcaggc ucaacagaga acagcug                  947
```

<210> SEQ ID NO 4
<211> LENGTH: 2705
<212> TYPE: DNA
<213> ORGANISM: Homo sapiens

<400> SEQUENCE: 4

```
aattttaata accactcact gaattaaaaa cctttctaat aaaggtaata taaatattaa     60

ttttattata cattgaaaat gagactcaaa attcttgact gggtcaaaat accatactag    120

aagcactgcc agtgtgctgg aattatgtca tatattgttt ctatattaaa aatcaaataa    180

aaaaccatca ggaatccagt gaaatggtta actcaaattc actattttat atgtgatttt    240

tttattttcc tcattacgta agcaggtatt ccccttccca aatctccttc ccaatggtac    300

ttacagagta ttcataattg tatctttaac tgcatatggt ggcacagaaa gccaaggact    360

gaacattctt atgatatcta ctgtatcgaa tgaatggcta atgtctaatt gcagaattaa    420
```

-continued

```
gtaggctgtg cttgtgccag ctgcttctcc attttatggg tttatttgac tgattattta    480
caagaaacac attaaaatgg catctattcc tcctgaaaac atgctggcat tagtcaatca    540
acagaattta accttaatag atactacagt ccagtaagta tggcatcaaa aaaatgagat    600
ggcagatacc aacagagcag catggtactt ccatgagaag gagccagtgt aagtcttaat    660
tcattaaata ttctgtttca tgggagttat gtagtaagtt tctgtaaagt aaagcaaatc    720
caatgctcta gttacaatga ttgagttaaa caaatacatt tctctaatat gcttttactc    780
caagcaacaa tttgcagaat cctgtgtcac ctaagactaa ctaaggaaga atgaaagtag    840
ctctttttct tttcctgaaa agaaaggatg tttccaggtc tacaactaca tttgaagggt    900
ggcaaagtgt tttgttaaag ttgctgttat agcatagaaa atctctagaa ttttttcaaa    960
gctgggagtg acaactactt caaggattgc gactcaaatg cctacaaaag ccaggtagat   1020
tacataaatg tgtgaagaac ctggtgtgag gtggtaggaa gctatggaga ctgtaacaaa   1080
catcatgcct aaatatataa aaattaatta tgttagacaa aaccagacac tgtatttcct   1140
tcagccctca gagtcctcag cctgccgatt tgaaactttt gatgctttgt ctaatcaacc   1200
tcttttatag ataaggaaac ttaagtccca agagatttaa gtggctttct cagtgacata   1260
actgagatga gaactgaaat atcctccatg tcacagatca agtttttttg ttcatcttta   1320
tttttagttg gatcaatgtg cttactcaat ccgacatgct aaggttgcca ctgtctaact   1380
tgttatctga aactgtgagt ttcagaatga tgacctactc cggagacaat accacagtta   1440
caaattcata tcaacttcct actgaacctt tttttaagac aaatcaattg agttgattta   1500
ctgaaaagta aataagaatg aaatgcttta aaataaactt tcagcaattc aaatggtgat   1560
acattatcaa tgcactggaa gaatctacca gccaaacatt acttaattaa cccaagccta   1620
aataatgact aacattttaa ggttttattt actgaataaa agttaagcaa tctgcagcaa   1680
gaattcttaa cctattttcc atttaaaaca cagttacatt ttaagattta aactatttta   1740
tatttgtaat aaacagttaa taaagtccat aattattcca tcagtttagt agaaagatga   1800
actcttctac ttccttttga agaaaaaaaa agcaaaaata caaatataag accacatttt   1860
agttagcttt cttggctaat aatttcctta ctaaaattac cttgcatgag taagtttacg   1920
taaacataac ttttgcatat gccagaatga tacatacttg aaaatgtgtc aagccactaa   1980
ccttataaaa tgtatgcttt atttcatctt tgttactttt catatgttcc tttatagttg   2040
aaggttttga ctgaagctat cacttcgcag aaacaaacgg atgaactact tagctattac   2100
aactagagat tcttttagcc caggtgtatt cctgatcatg ttctccattt catgtaagct   2160
ttcctttttt cctgagatct tattaatttt ttacatatag gtaagcagcc ccatttctaa   2220
agtactgatt aacccaaagt cattaaggta gctctgtcta ccttagcaaa gcctggaatt   2280
tttgcataat aatgacgctt atgaattcca gggctacaac acttttctat aaagaaactt   2340
gtactgtaca gaaggtattt ttttattcta aattgctaat aaccactctc tcctcctacc   2400
tcataaaagc atatacatca gtagatgtat atttctgttt tagctgcatg gaccactgat   2460
gatggtcatg gttttatatt aagcttacat ttcctataat aaaaaaagat aacacaaatg   2520
caaggaaatt aaaaaaagga ggggtgttcc tgaatccaca gttatacaaa aatgatgaga   2580
gaatacaatg aagatggaag aaaacttcaa aatggagatc tgttaaatgt ccaaaggagg   2640
agacgattat taactctgca tggaaagcca tacttagaat tttctcactc ttcaaatccc   2700
agagt                                                               2705
```

<210> SEQ ID NO 5
<211> LENGTH: 2395
<212> TYPE: DNA
<213> ORGANISM: Homo sapiens

<400> SEQUENCE: 5

```
cctaagattc agtcaccatc tcggttcctt ttcactcttc taaaatttta gatatgcttg     60
gtataaagaa aaaaacaaac tattcatcaa acttttttca tcaggatgtt tatgcttatt    120
tggtgggact taaagcctcc acaactccta gcttatttga aataggcttc agagacacca    180
ggctaaacat tattaaatta caagagtaac atcttttccg tggactttta tccaattctg    240
cccatccaca ttcaggtcct tacatattac caacctaagg tctccagggc agccaccatg    300
ggggtgtgcc ctccagggtt ccagaaatgt attcacgggg cacaaaagat tttgtgctg     360
aggctaggga tccaattagc tatgaaacat acttccgtat gctcgttgga aataaaaaaa    420
gtttcataat tcccttctat ggaaattttc tttgtgactt ctaatatact tatataatat    480
caacaggata atgcgatatt atccattaaa gctacaatat gtggccatag agacatatgg    540
taactaaatc caagcagcag ctgtaagtct tctttcaagc tacttcctgt atctgagatt    600
tacctcagat tctgaaaggt ttatggcaat gttcaagatg ccaaaaatcc attaacagta    660
tgaaattatt accttctgga ttttactgct catcgtgatc atctttcaga atcaagtgct    720
tgaaataagc acaattaaaa ttttaatcag tcacctgtag ctgttgaaag ggcagaagtt    780
cttcctgatg gtgataataa tagtatgtca taataagaac aatgaaagtt gtattaaaag    840
aaaaatacca gctgttctct gttgagcctg cttctgcgtg gaccttcagg aatttcatac    900
ttttcttcct gttcacatac ttttcttcgt agacatgctt ttacccctga caaaaacaca    960
agaattaaag caaactaagt atcaagtgag cactatatct ctctcattaa aatcaagcaa   1020
tttacctaag tggtttttct tcttcatggc agtttttaag tattattcta aaatgcaaac   1080
agaaatctta cttatgccaa aacaaaatgt aatacaactg gttttcccat ataaagaaaa   1140
tattttaaaa aactctttct ttggaggatt aagccataag ttagtactga acactaactg   1200
taattttaat ctcctttctg aaaaacctaa gccaggatac tatttcaaag acaaaaataa   1260
aagtctacat ttccactcat agcaattacc caaaattaag gtgaataaaa agtccatgac   1320
acaataacct aaactgagca cttaccatct atactgctca ttttgacagt tatatgtcta   1380
atcgtctgtt aaactgtaag tgatttgaca tgaaggaatg tgctttagtc tacagcacca   1440
agctcagcta gccacacaac aggggttcaa cagcgcttcc taaaataaac aagcagagct   1500
tgggataggt ttggcatgtg acaggtacac aactgaggtt gctagtctag agatgatttg   1560
attgggcttt gcaggaaaaa aaaaagcatt cttttgatgg cttgagtaag tctgttcaca   1620
gcttcaggtt aaaaagcaaa agcaatagag acagctcagc ctggcactgt ttagagtcat   1680
tccactgctt ggcacctggg tggggaatcc ctaagtaggg ccactggctg gcagccagta   1740
ccaattgtct cgctaggctc tagaaatgaa aggaaccctt gggattccca ggaccaatca   1800
tgaaggacat ggtcagcttc agctagagac aacatcttgg ataatgcctg tttaccacca   1860
agcgagggaa ctgatggcat gtatatatat ttatcatgct tctgttctga tggcatataa   1920
ctaaactaaa tttgagattt gcagttgaag gacttggcta tcccaattac ttgttctgga   1980
agcttccttg cctatggaaa taaaaaatga aaacaatgtt tttcaccggg cttctgtgga   2040
taaaatgcaa gaagcattct aaaaactaga tactacaatg aattatcttc atcataaaaa   2100
caaaccctcc atacaatttc ctatttgtct ttgaggttgt tttgctcaat acttcatttt   2160
```

```
atcactgagg gtaggaacca tatattattc acctatgcgt tcttcagaat ttcatacact    2220

ttcccataga acaggagttt aatagcagag ggtatcggga aagttggaac aataactcag    2280

gtatcccctt cactgtctag tgttgttaac ataaaggaac aaaagttttt aaaaattcac    2340

tatggacaca gcattgacag attgtatcca catcaataaa aataagtaat tatat          2395
```

<210> SEQ ID NO 6
<211> LENGTH: 21
<212> TYPE: DNA
<213> ORGANISM: Artificial
<220> FEATURE:
<223> OTHER INFORMATION: siRNA 1 sense

<400> SEQUENCE: 6
caaggguucc uuucauuuct t    21

<210> SEQ ID NO 7
<211> LENGTH: 21
<212> TYPE: DNA
<213> ORGANISM: Artificial
<220> FEATURE:
<223> OTHER INFORMATION: siRNA 1 antisense

<400> SEQUENCE: 7
gaaaugaaag gaacccuugt t    21

<210> SEQ ID NO 8
<211> LENGTH: 21
<212> TYPE: DNA
<213> ORGANISM: Artificial
<220> FEATURE:
<223> OTHER INFORMATION: siRNA 2 sense

<400> SEQUENCE: 8
aaggguuccu uucauuucut t    21

<210> SEQ ID NO 9
<211> LENGTH: 21
<212> TYPE: DNA
<213> ORGANISM: Artificial
<220> FEATURE:
<223> OTHER INFORMATION: siRNA 2 antisense

<400> SEQUENCE: 9
agaaaugaaa ggaacccuut t    21

<210> SEQ ID NO 10
<211> LENGTH: 21
<212> TYPE: DNA
<213> ORGANISM: Artificial
<220> FEATURE:
<223> OTHER INFORMATION: siRNA 3 sense

<400> SEQUENCE: 10
aggguuccuu ucauuucuat t    21

<210> SEQ ID NO 11
<211> LENGTH: 21
<212> TYPE: DNA
<213> ORGANISM: Artificial
<220> FEATURE:
<223> OTHER INFORMATION: siRNA 3 antisense

<400> SEQUENCE: 11
uagaaaugaa aggaacccut t    21

<210> SEQ ID NO 12
<211> LENGTH: 21
<212> TYPE: DNA
<213> ORGANISM: Artificial
<220> FEATURE:
<223> OTHER INFORMATION: siRNA 4 sense

<400> SEQUENCE: 12
uagagccuag cgagacaaut t 21

<210> SEQ ID NO 13
<211> LENGTH: 21
<212> TYPE: DNA
<213> ORGANISM: Artificial
<220> FEATURE:
<223> OTHER INFORMATION: siRNA 4 antisense

<400> SEQUENCE: 13
auugucucgc uaggcucuat t 21

<210> SEQ ID NO 14
<211> LENGTH: 21
<212> TYPE: DNA
<213> ORGANISM: Artificial
<220> FEATURE:
<223> OTHER INFORMATION: siRNA 5 sense

<400> SEQUENCE: 14
agagccuagc gagacaauut t 21

<210> SEQ ID NO 15
<211> LENGTH: 21
<212> TYPE: DNA
<213> ORGANISM: Artificial
<220> FEATURE:
<223> OTHER INFORMATION: siRNA 5 antisense

<400> SEQUENCE: 15
aauugucucg cuaggcucut t 21

<210> SEQ ID NO 16
<211> LENGTH: 21
<212> TYPE: DNA
<213> ORGANISM: Artificial
<220> FEATURE:
<223> OTHER INFORMATION: siRNA 6 sense

<400> SEQUENCE: 16
uggaaugacu cuaaacagut t 21

<210> SEQ ID NO 17
<211> LENGTH: 21
<212> TYPE: DNA
<213> ORGANISM: Artificial
<220> FEATURE:
<223> OTHER INFORMATION: siRNA 6 antisense

<400> SEQUENCE: 17
acuguuuaga gucauuccat t 21

<210> SEQ ID NO 18
<211> LENGTH: 21
<212> TYPE: DNA
<213> ORGANISM: Artificial
<220> FEATURE:

-continued

<223> OTHER INFORMATION: siRNA 7 sense

<400> SEQUENCE: 18
ggaaugacuc uaaacagugt t 21

<210> SEQ ID NO 19
<211> LENGTH: 21
<212> TYPE: DNA
<213> ORGANISM: Artificial
<220> FEATURE:
<223> OTHER INFORMATION: siRNA 7 antisense

<400> SEQUENCE: 19
cacuguuuag agucauucct t 21

<210> SEQ ID NO 20
<211> LENGTH: 21
<212> TYPE: DNA
<213> ORGANISM: Artificial
<220> FEATURE:
<223> OTHER INFORMATION: siRNA 8 sense

<400> SEQUENCE: 20
uaaccugaag cugugaacat t 21

<210> SEQ ID NO 21
<211> LENGTH: 21
<212> TYPE: DNA
<213> ORGANISM: Artificial
<220> FEATURE:
<223> OTHER INFORMATION: siRNA 8 antisense

<400> SEQUENCE: 21
uguucacagc uucagguuat t 21

<210> SEQ ID NO 22
<211> LENGTH: 21
<212> TYPE: DNA
<213> ORGANISM: Artificial
<220> FEATURE:
<223> OTHER INFORMATION: siRNA 9 sense

<400> SEQUENCE: 22
agcccaauca aaucaucuct t 21

<210> SEQ ID NO 23
<211> LENGTH: 21
<212> TYPE: DNA
<213> ORGANISM: Artificial
<220> FEATURE:
<223> OTHER INFORMATION: siRNA 9 antisense

<400> SEQUENCE: 23
gagaugauuu gauugggcut t 21

<210> SEQ ID NO 24
<211> LENGTH: 21
<212> TYPE: DNA
<213> ORGANISM: Artificial
<220> FEATURE:
<223> OTHER INFORMATION: siRNA 10 sense
<220> FEATURE:
<221> NAME/KEY: misc_feature
<222> LOCATION: (20)..(21)
<223> OTHER INFORMATION: may be uu

<400> SEQUENCE: 24

-continued gcccaaucaa aucaucucut t 21

<210> SEQ ID NO 25
<211> LENGTH: 21
<212> TYPE: DNA
<213> ORGANISM: Artificial
<220> FEATURE:
<223> OTHER INFORMATION: siRNA 10 antisense

<400> SEQUENCE: 25
agagaugauu ugauugggct t 21

<210> SEQ ID NO 26
<211> LENGTH: 21
<212> TYPE: DNA
<213> ORGANISM: Artificial
<220> FEATURE:
<223> OTHER INFORMATION: siRNA 11 sense

<400> SEQUENCE: 26
cccaaucaaa ucaucucuat t 21

<210> SEQ ID NO 27
<211> LENGTH: 21
<212> TYPE: DNA
<213> ORGANISM: Artificial
<220> FEATURE:
<223> OTHER INFORMATION: siRNA 11 antisense

<400> SEQUENCE: 27
uagagaugau uugauugggt t 21

<210> SEQ ID NO 28
<211> LENGTH: 21
<212> TYPE: DNA
<213> ORGANISM: Artificial
<220> FEATURE:
<223> OTHER INFORMATION: siRNA 12 sense

<400> SEQUENCE: 28
uaccugucac augccaaact t 21

<210> SEQ ID NO 29
<211> LENGTH: 21
<212> TYPE: DNA
<213> ORGANISM: Artificial
<220> FEATURE:
<223> OTHER INFORMATION: siRNA 12 antisense

<400> SEQUENCE: 29
guuuggcaug ugacagguat t 21

<210> SEQ ID NO 30
<211> LENGTH: 21
<212> TYPE: DNA
<213> ORGANISM: Artificial
<220> FEATURE:
<223> OTHER INFORMATION: siRNA 13 sense

<400> SEQUENCE: 30
accugucaca ugccaaacct t 21

<210> SEQ ID NO 31
<211> LENGTH: 21
<212> TYPE: DNA

<213> ORGANISM: Artificial
<220> FEATURE:
<223> OTHER INFORMATION: siRNA 13 antisense

<400> SEQUENCE: 31
gguuuggcau gugacaggut t 21

<210> SEQ ID NO 32
<211> LENGTH: 21
<212> TYPE: DNA
<213> ORGANISM: Artificial
<220> FEATURE:
<223> OTHER INFORMATION: siRNA 14 sense

<400> SEQUENCE: 32
ucacaugcca aaccuaucct t 21

<210> SEQ ID NO 33
<211> LENGTH: 21
<212> TYPE: DNA
<213> ORGANISM: Artificial
<220> FEATURE:
<223> OTHER INFORMATION: siRNA 14 antisense

<400> SEQUENCE: 33
ggauagguuu ggcaugugat t 21

<210> SEQ ID NO 34
<211> LENGTH: 21
<212> TYPE: DNA
<213> ORGANISM: Artificial
<220> FEATURE:
<223> OTHER INFORMATION: siRNA 15 sense

<400> SEQUENCE: 34
caugccaaac cuaucccaat t 21

<210> SEQ ID NO 35
<211> LENGTH: 21
<212> TYPE: DNA
<213> ORGANISM: Artificial
<220> FEATURE:
<223> OTHER INFORMATION: siRNA 15 antisense

<400> SEQUENCE: 35
uugggauagg uuuggcaugt t 21

<210> SEQ ID NO 36
<211> LENGTH: 21
<212> TYPE: DNA
<213> ORGANISM: Artificial
<220> FEATURE:
<223> OTHER INFORMATION: siRNA 16 sense

<400> SEQUENCE: 36
gcuuggugcu guagacuaat t 21

<210> SEQ ID NO 37
<211> LENGTH: 21
<212> TYPE: DNA
<213> ORGANISM: Artificial
<220> FEATURE:
<223> OTHER INFORMATION: siRNA 16 antisense

<400> SEQUENCE: 37
uuagucuaca gcaccaagct t 21

<210> SEQ ID NO 38
<211> LENGTH: 21
<212> TYPE: DNA
<213> ORGANISM: Artificial
<220> FEATURE:
<223> OTHER INFORMATION: siRNA17 sense

<400> SEQUENCE: 38
cuuggugcug uagacuaaat t 21

<210> SEQ ID NO 39
<211> LENGTH: 21
<212> TYPE: DNA
<213> ORGANISM: Artificial
<220> FEATURE:
<223> OTHER INFORMATION: siRNA 17 antisense

<400> SEQUENCE: 39
uuuagucuac agcaccaagt t 21

<210> SEQ ID NO 40
<211> LENGTH: 21
<212> TYPE: DNA
<213> ORGANISM: Artificial
<220> FEATURE:
<223> OTHER INFORMATION: siRNA 18 sense

<400> SEQUENCE: 40
guagacuaaa gcacauucct t 21

<210> SEQ ID NO 41
<211> LENGTH: 21
<212> TYPE: DNA
<213> ORGANISM: Artificial
<220> FEATURE:
<223> OTHER INFORMATION: siRNA 18 antisense

<400> SEQUENCE: 41
ggaaugugcu uuagucuact t 21

<210> SEQ ID NO 42
<211> LENGTH: 21
<212> TYPE: DNA
<213> ORGANISM: Artificial
<220> FEATURE:
<223> OTHER INFORMATION: siRNA 19 sense

<400> SEQUENCE: 42
uagacuaaag cacauuccut t 21

<210> SEQ ID NO 43
<211> LENGTH: 21
<212> TYPE: DNA
<213> ORGANISM: Artificial
<220> FEATURE:
<223> OTHER INFORMATION: siRNA 19 antisense

<400> SEQUENCE: 43
aggaaugugc uuuagucuat t 21

<210> SEQ ID NO 44
<211> LENGTH: 21
<212> TYPE: DNA
<213> ORGANISM: Artificial
<220> FEATURE:

<223> OTHER INFORMATION: siRNA 20 sense

<400> SEQUENCE: 44
cauuccuuca ugucaaauct t 21

<210> SEQ ID NO 45
<211> LENGTH: 21
<212> TYPE: DNA
<213> ORGANISM: Artificial
<220> FEATURE:
<223> OTHER INFORMATION: siRNA 20 antisense

<400> SEQUENCE: 45
gauuugacau gaaggaaugt t 21

<210> SEQ ID NO 46
<211> LENGTH: 21
<212> TYPE: DNA
<213> ORGANISM: Artificial
<220> FEATURE:
<223> OTHER INFORMATION: siRNA 21 sense

<400> SEQUENCE: 46
auuccuucau gucaaaucat t 21

<210> SEQ ID NO 47
<211> LENGTH: 21
<212> TYPE: DNA
<213> ORGANISM: Artificial
<220> FEATURE:
<223> OTHER INFORMATION: siRNA 21 antisense

<400> SEQUENCE: 47
ugauuugaca ugaaggaaut t 21

<210> SEQ ID NO 48
<211> LENGTH: 21
<212> TYPE: DNA
<213> ORGANISM: Artificial
<220> FEATURE:
<223> OTHER INFORMATION: siRNA 22 sense

<400> SEQUENCE: 48
ccuucauguc aaaucacuut t 21

<210> SEQ ID NO 49
<211> LENGTH: 21
<212> TYPE: DNA
<213> ORGANISM: Artificial
<220> FEATURE:
<223> OTHER INFORMATION: siRNA 22 antisense

<400> SEQUENCE: 49
aagugauuug acaugaaggt t 21

<210> SEQ ID NO 50
<211> LENGTH: 21
<212> TYPE: DNA
<213> ORGANISM: Artificial
<220> FEATURE:
<223> OTHER INFORMATION: siRNA 23 sense

<400> SEQUENCE: 50
guucaguacu aacuuauggt t 21

<210> SEQ ID NO 51
<211> LENGTH: 21
<212> TYPE: DNA
<213> ORGANISM: Artificial
<220> FEATURE:
<223> OTHER INFORMATION: siRNA 23 antisense

<400> SEQUENCE: 51
ccauaaguua guacugaact t 21

<210> SEQ ID NO 52
<211> LENGTH: 21
<212> TYPE: DNA
<213> ORGANISM: Artificial
<220> FEATURE:
<223> OTHER INFORMATION: siRNA 24 sense

<400> SEQUENCE: 52
guaagauuuc uguuugcaut t 21

<210> SEQ ID NO 53
<211> LENGTH: 21
<212> TYPE: DNA
<213> ORGANISM: Artificial
<220> FEATURE:
<223> OTHER INFORMATION: siRNA24 antisense

<400> SEQUENCE: 53
augcaaacag aaaucuuact t 21

<210> SEQ ID NO 54
<211> LENGTH: 21
<212> TYPE: DNA
<213> ORGANISM: Artificial
<220> FEATURE:
<223> OTHER INFORMATION: siRNA 25 sense

<400> SEQUENCE: 54
aaaccacuua gguaaauugt t 21

<210> SEQ ID NO 55
<211> LENGTH: 21
<212> TYPE: DNA
<213> ORGANISM: Artificial
<220> FEATURE:
<223> OTHER INFORMATION: siRNA 25 antisense

<400> SEQUENCE: 55
caauuuaccu aagugguuut t 21

<210> SEQ ID NO 56
<211> LENGTH: 21
<212> TYPE: DNA
<213> ORGANISM: Artificial
<220> FEATURE:
<223> OTHER INFORMATION: siRNA 26 sense

<400> SEQUENCE: 56
aaccacuuag guaaauugct t 21

<210> SEQ ID NO 57
<211> LENGTH: 21
<212> TYPE: DNA
<213> ORGANISM: Artificial
<220> FEATURE:
<223> OTHER INFORMATION: siRNA 26 antisense

```
<400> SEQUENCE: 57

gcaauuuacc uaaguggUUt t                                              21

<210> SEQ ID NO 58
<211> LENGTH: 21
<212> TYPE: DNA
<213> ORGANISM: Artificial
<220> FEATURE:
<223> OTHER INFORMATION: siRNA 27 sense

<400> SEQUENCE: 58

uagugcucac uugauacuut t                                              21

<210> SEQ ID NO 59
<211> LENGTH: 21
<212> TYPE: DNA
<213> ORGANISM: Artificial
<220> FEATURE:
<223> OTHER INFORMATION: siRNA 27 antisense

<400> SEQUENCE: 59

aaguaucaag ugagcacuat t                                              21

<210> SEQ ID NO 60
<211> LENGTH: 21
<212> TYPE: DNA
<213> ORGANISM: Artificial
<220> FEATURE:
<223> OTHER INFORMATION: siRNA 28 sense

<400> SEQUENCE: 60

cucacuugau acuuaguuut t                                              21

<210> SEQ ID NO 61
<211> LENGTH: 21
<212> TYPE: DNA
<213> ORGANISM: Artificial
<220> FEATURE:
<223> OTHER INFORMATION: siRNA 28 antisense

<400> SEQUENCE: 61

aaacuaagua ucaagugagt t                                              21

<210> SEQ ID NO 62
<211> LENGTH: 21
<212> TYPE: DNA
<213> ORGANISM: Artificial
<220> FEATURE:
<223> OTHER INFORMATION: siRNA 29 sense

<400> SEQUENCE: 62

ucacuugaua cuuaguuugt t                                              21

<210> SEQ ID NO 63
<211> LENGTH: 21
<212> TYPE: DNA
<213> ORGANISM: Artificial
<220> FEATURE:
<223> OTHER INFORMATION: siRNA29 antisense

<400> SEQUENCE: 63

caaacuaagu aucaagugat t                                              21

<210> SEQ ID NO 64
<211> LENGTH: 21
```

<212> TYPE: DNA
<213> ORGANISM: Artificial
<220> FEATURE:
<223> OTHER INFORMATION: siRNA 30 sense

<400> SEQUENCE: 64
cuugauacuu aguuugcuut t 21

<210> SEQ ID NO 65
<211> LENGTH: 21
<212> TYPE: DNA
<213> ORGANISM: Artificial
<220> FEATURE:
<223> OTHER INFORMATION: siRNA 30 antisense

<400> SEQUENCE: 65
aagcaaacua aguaucaagt t 21

<210> SEQ ID NO 66
<211> LENGTH: 20
<212> TYPE: DNA
<213> ORGANISM: Artificial
<220> FEATURE:
<223> OTHER INFORMATION: Primer pATG_F

<400> SEQUENCE: 66
atgccggata atcggcagcc 20

<210> SEQ ID NO 67
<211> LENGTH: 19
<212> TYPE: DNA
<213> ORGANISM: Artificial
<220> FEATURE:
<223> OTHER INFORMATION: Primer p8_F

<400> SEQUENCE: 67
agggatggac ctcttgtac 19

<210> SEQ ID NO 68
<211> LENGTH: 20
<212> TYPE: DNA
<213> ORGANISM: Artificial
<220> FEATURE:
<223> OTHER INFORMATION: Primer p6_F

<400> SEQUENCE: 68
ctccagcata aggcattggt 20

<210> SEQ ID NO 69
<211> LENGTH: 20
<212> TYPE: DNA
<213> ORGANISM: Artificial
<220> FEATURE:
<223> OTHER INFORMATION: Primer p11_R1

<400> SEQUENCE: 69
cgaaccctct ctgggtgata 20

<210> SEQ ID NO 70
<211> LENGTH: 21
<212> TYPE: DNA
<213> ORGANISM: Artificial
<220> FEATURE:
<223> OTHER INFORMATION: Primer p11_R2

<400> SEQUENCE: 70
cagctgtcaa gaggaagcaa c 21

<210> SEQ ID NO 71
<211> LENGTH: 22
<212> TYPE: DNA
<213> ORGANISM: Artificial
<220> FEATURE:
<223> OTHER INFORMATION: Primer p11_R3

<400> SEQUENCE: 71
catgataaat caaaaacatg cc 22

<210> SEQ ID NO 72
<211> LENGTH: 24
<212> TYPE: DNA
<213> ORGANISM: Artificial
<220> FEATURE:
<223> OTHER INFORMATION: Primer p11_R4

<400> SEQUENCE: 72
aagggttgac ttataaagaa atac 24

<210> SEQ ID NO 73
<211> LENGTH: 25
<212> TYPE: DNA
<213> ORGANISM: Artificial
<220> FEATURE:
<223> OTHER INFORMATION: Primer p11_R5

<400> SEQUENCE: 73
caacttctca atatttattt attca 25

<210> SEQ ID NO 74
<211> LENGTH: 25
<212> TYPE: DNA
<213> ORGANISM: Artificial
<220> FEATURE:
<223> OTHER INFORMATION: Primer p11_R6

<400> SEQUENCE: 74
gccaggcata agactattag ttgac 25

<210> SEQ ID NO 75
<211> LENGTH: 20
<212> TYPE: DNA
<213> ORGANISM: Artificial
<220> FEATURE:
<223> OTHER INFORMATION: Primer p9'_F1

<400> SEQUENCE: 75
cctgggaatc ccaagggttc 20

<210> SEQ ID NO 76
<211> LENGTH: 25
<212> TYPE: DNA
<213> ORGANISM: Artificial
<220> FEATURE:
<223> OTHER INFORMATION: Primer p9'_F2

<400> SEQUENCE: 76
caaatcactt acagtttaac agacg 25

<210> SEQ ID NO 77
<211> LENGTH: 21
<212> TYPE: DNA
<213> ORGANISM: Artificial

```
<220> FEATURE:
<223> OTHER INFORMATION: Primer BARD1beta Junct ex1-4

<400> SEQUENCE: 77

ctgctcgcgt tgatttgaaa g                                              21


<210> SEQ ID NO 78
<211> LENGTH: 20
<212> TYPE: DNA
<213> ORGANISM: Artificial
<220> FEATURE:
<223> OTHER INFORMATION: Primer BARD1gamma Junct ex3-5

<400> SEQUENCE: 78

caatgagctg tcagggcgac                                                20


<210> SEQ ID NO 79
<211> LENGTH: 22
<212> TYPE: DNA
<213> ORGANISM: Artificial
<220> FEATURE:
<223> OTHER INFORMATION: Primer BARD1delta Junct ex1-7

<400> SEQUENCE: 79

tgctcgcgtt gtaatatatt tg                                             22


<210> SEQ ID NO 80
<211> LENGTH: 24
<212> TYPE: DNA
<213> ORGANISM: Artificial
<220> FEATURE:
<223> OTHER INFORMATION: Primer 5'RACE GSP1

<400> SEQUENCE: 80

ctgttaaact gtaagtgatt tgac                                           24


<210> SEQ ID NO 81
<211> LENGTH: 25
<212> TYPE: DNA
<213> ORGANISM: Artificial
<220> FEATURE:
<223> OTHER INFORMATION: Primer 5'RACE GSP2

<400> SEQUENCE: 81

ccaagctcag ctagccacac aacag                                          25


<210> SEQ ID NO 82
<211> LENGTH: 22
<212> TYPE: RNA
<213> ORGANISM: Artificial
<220> FEATURE:
<223> OTHER INFORMATION: microRNA hsa-miR-513c

<400> SEQUENCE: 82

uauuugcugu ggaggaacuc uu                                             22


<210> SEQ ID NO 83
<211> LENGTH: 40
<212> TYPE: DNA
<213> ORGANISM: Homo sapiens

<400> SEQUENCE: 83

tgagtgggca ggataccacy tgagagtggc cagatgtggg                          40


<210> SEQ ID NO 84
```

<211> LENGTH: 22
<212> TYPE: RNA
<213> ORGANISM: Artificial
<220> FEATURE:
<223> OTHER INFORMATION: micro RNA hsa-miR-514b-5p

<400> SEQUENCE: 84
uacuaacgga gggagaacuc uu 22

<210> SEQ ID NO 85
<211> LENGTH: 21
<212> TYPE: RNA
<213> ORGANISM: Artificial
<220> FEATURE:
<223> OTHER INFORMATION: microRNA hsa-miR-588

<400> SEQUENCE: 85
caagauuggg uaacaccggu u 21

<210> SEQ ID NO 86
<211> LENGTH: 23
<212> TYPE: RNA
<213> ORGANISM: Artificial
<220> FEATURE:
<223> OTHER INFORMATION: microRNA hsa-miR-668

<400> SEQUENCE: 86
caucacccgg cucggcucac ugu 23

<210> SEQ ID NO 87
<211> LENGTH: 43
<212> TYPE: DNA
<213> ORGANISM: Homo sapiens

<400> SEQUENCE: 87
ccccacatct ggccactctc aggtggtatc ctgcccactc act 43

<210> SEQ ID NO 88

<400> SEQUENCE: 88

000

<210> SEQ ID NO 89
<211> LENGTH: 42
<212> TYPE: DNA
<213> ORGANISM: Rhesus

<400> SEQUENCE: 89
cccaggtctg gccactctca cgtggtatcc cgcccactca ct 42

<210> SEQ ID NO 90
<211> LENGTH: 42
<212> TYPE: DNA
<213> ORGANISM: Baboon

<400> SEQUENCE: 90
cccaggtctg gccactctca cgtggtatcc cgcccactca ct 42

<210> SEQ ID NO 91
<211> LENGTH: 43
<212> TYPE: DNA
<213> ORGANISM: Cow

<400> SEQUENCE: 91
ccccaggtct ccccattctc agaagatgtc ctgtccacta ctt 43

<210> SEQ ID NO 92
<211> LENGTH: 43
<212> TYPE: DNA
<213> ORGANISM: Domestic goat

<400> SEQUENCE: 92
tcccaggtct ccccattctc agaagatgtc ctgtccacta ctc 43

<210> SEQ ID NO 93
<211> LENGTH: 43
<212> TYPE: DNA
<213> ORGANISM: Cat

<400> SEQUENCE: 93
cccccaggcc tcccgttctc aggtggtgtc ctgtccactc ttc 43

<210> SEQ ID NO 94
<211> LENGTH: 40
<212> TYPE: DNA
<213> ORGANISM: Mouse

<400> SEQUENCE: 94
gcagtgtgcg caggctcagg caatgctctc cctacttcac 40

<210> SEQ ID NO 95
<211> LENGTH: 38
<212> TYPE: DNA
<213> ORGANISM: Rat

<400> SEQUENCE: 95
tccagtgtgc gcatgctcag gagtgccccc cacacccc 38

<210> SEQ ID NO 96
<211> LENGTH: 33
<212> TYPE: DNA
<213> ORGANISM: Rabbit

<400> SEQUENCE: 96
ccccattccc aggaggagca ctgtccgcca ctc 33

<210> SEQ ID NO 97
<211> LENGTH: 43
<212> TYPE: DNA
<213> ORGANISM: Guinea pig

<400> SEQUENCE: 97
gctcggcaca ggccactttc aagctgcgct ctgtccaaca ctt 43

<210> SEQ ID NO 98
<211> LENGTH: 44
<212> TYPE: DNA
<213> ORGANISM: Pig

<400> SEQUENCE: 98
ccccaggtct ccctgttttc acttgatatt ctacctatta cctt 44

<210> SEQ ID NO 99
<211> LENGTH: 17
<212> TYPE: DNA
<213> ORGANISM: Horse

<400> SEQUENCE: 99
cccagccccg cctgctc 17

<210> SEQ ID NO 100
<211> LENGTH: 42
<212> TYPE: DNA
<213> ORGANISM: Artificial
<220> FEATURE:
<223> OTHER INFORMATION: Consensus sequence of BARD1 3'UTR

<400> SEQUENCE: 100
ccccaggtct cgccactctc aggtggtgtc ctgccactcc tt 42

<210> SEQ ID NO 101
<211> LENGTH: 12
<212> TYPE: PRT
<213> ORGANISM: Homo sapiens

<400> SEQUENCE: 101

Met Ser Ser Ile Asp Gly Val Lys Ala Cys Leu Arg
1 5 10

<210> SEQ ID NO 102
<211> LENGTH: 39
<212> TYPE: DNA
<213> ORGANISM: Homo sapiens

<400> SEQUENCE: 102
aaaatgagca gtatagatgg ggtaaaagca tgtctacga 39

<210> SEQ ID NO 103
<211> LENGTH: 22
<212> TYPE: RNA
<213> ORGANISM: Artificial
<220> FEATURE:
<223> OTHER INFORMATION: microRNA miR-203

<400> SEQUENCE: 103
gaucaccagg auuuguaaag ug 22

<210> SEQ ID NO 104
<211> LENGTH: 21
<212> TYPE: RNA
<213> ORGANISM: Artificial
<220> FEATURE:
<223> OTHER INFORMATION: microRNA miR-101

<400> SEQUENCE: 104
aagucaauag ugucaugaca u 21

<210> SEQ ID NO 105
<211> LENGTH: 253
<212> TYPE: RNA
<213> ORGANISM: Homo sapiens

<400> SEQUENCE: 105
auauuauacc agaugaacau uucaaauuga auuugcacgg uuugugagag cccagucauu 60
guacuguuuu uaauguucac auuuuuacaa auagguagag ucauucauau uugucuuuga 120
aucaaaaaaa aaaaaaaaag ucuaaugcca gauuaggaau ucauguugug uuuaccauuu 180
agaagcuggg auugcuuuua aagguuuuuc uuuuuaaaau uggcauguuu uugauuuauc 240
augucuuucu auu 253

REGULATION OF BARD1 EXPRESSION BY NON-CODING RNA

CROSS REFERENCE TO RELATED APPLICATIONS

The present application claims priority to European Patent Application No. 14002398.7, filed on Jul. 12, 2014.

SEQUENCE LISTING

The present application includes a Sequence Listing in electronic format. The Sequence Listing is entitled 4472105SequenceListingRev.txt, was created on 21 Feb. 2018 and is 33 kb in size. The information in the electronic format of the Sequence Listing is part of the present application and is incorporated herein by reference in its entirety.

TECHNICAL FIELD

The invention relates to novel non-coding RNA and compounds for cancer treatment.

BACKGROUND OF THE INVENTION

Long non-coding RNAs (lncRNAs) are ubiquitously expressed RNA molecules of more than 200 nucleotides without substantial ORFs. LncRNAs could act as epigenetic regulators of gene expression affecting transcription, mRNA stability and transport, and translation, although, precise functions have been attributed to only few of them. Competing endogenous RNAs (ceRNAs) represent one recently emerged type of functional lncRNAs that share microRNA recognition sequences with mRNAs and may compete for microRNA binding and thus affect regulation and function of target mRNAs. We studied the epigenetic regulation of the BARD1 gene. The BARD1 protein acts as tumor suppressor with BRCA1. In cancer, mRNAs encoding the tumor suppressor full length BARD1 are often down-regulated while the expression of oncogenic truncated isoforms is boosted. We found that the BARD1 3'UTR is almost 3000 nt long and harbors a large number of microRNA binding elements. In addition we discovered a novel lncRNA, BARD1 9'L, which is transcribed from an alternative promoter in intron 9 of the BARD1 gene and shares part of the 3'UTR with the protein coding BARD1 mRNAs. We demonstrate with the example of two microRNAs, miR-203 and miR-101, that they down-regulate the expression of FL BARD1 and cancer-associated BARD1 mRNAs, and that BARD1 9'L counteracts the effect of miR-203 and miR-101, As BARD1 9'L is abnormally over-expressed in human cancers, we suggest it might be a tumor promoting factor and treatment target.

Long non coding RNAs (lncRNA) are RNA molecules longer than 200 nucleotides and without substantial ORFs that may encode polypeptides (Kapranov et al. 2007; Dinger et al. 2009). The GENCODE consortium working within the framework of the ENCODE project recently presented the annotation of human lncRNAs, including 9277 genes which produce 14,880 transcripts (Derrien et al. 2012). Interestingly, they demonstrated that lncRNAs coding genes have histone-modification profiles, splicing signals, and exon/intron lengths similar to that of protein-coding genes. LncRNAs may also be polyadenylated and share exon sequences with the protein coding genes (Carninci et al. 2005; Derrien et al. 2012). LncRNAs are found in the nucleus as well as in the cytosol, and many lncRNAs are tissue specifically expressed (Carninci et al. 2005; Birney et al. 2007; Derrien et al. 2012). Despite the ubiquitous presence and abundant expression of lncRNAs, a function was attributed to only few of them.

LncRNAs are involved in the epigenetic regulation of gene expression, as was shown with the examples of the regulation of the HOXC gene by antisense HOX intergenic RNA (HOTAIR) (He et al. 2011) and X chromosome inactivation in female mammals mediated by the inactive X-specific transcript (XIST) (Brown et al. 1991). LncRNAs may also play a role in a variety of cellular processes including transcription regulation, alternative splicing, RNA decay, nuclear import, and translation (Ponting et al. 2009; Wilusz et al. 2009; Wapinski and Chang 2011).

Competing endogenous RNAs (ceRNA) represent one of the recently emerged types of functional lncRNAs. It has been shown that lncRNAs that share microRNA recognition elements (MRE) with specific mRNAs may compete for microRNA binding and thus affect the function of these mRNAs. The striking example of such a competing endogenous RNA (ceRNA) is a ~500 nt lncRNA first identified as the most up-regulated gene in hepatocellular carcinoma and colorectal cancers (Panzitt et al. 2007; Matouk et al. 2009). This RNA, termed HULC (highly up-regulated in liver cancer), is polyadenylated and consists of two exons. It inhibits the activity and competes for binding of miR-372 and reduces the activity of its target gene PRKACB (Wang et al. 2010). Similar to HULC, the non-coding PTENP1 pseudogene RNA, regulates tumor suppressor gene PTEN acting as ceRNA (Poliseno et al. 2010). PTENP1 mRNA shares homology with the PTEN mRNA 3'UTR and competes for microRNAs that down-regulates PTEN expression. Knockdown of endogenous PTENP1 in prostate cancer cells results in an increase in PTEN mRNA and protein levels and those of the miR-17-5 p/20 target p21 and potentially other relevant targets. A similar correlation of expression is found between KRAS and its pseudogene KRAS1P (Poliseno et al. 2010). It was suggested that protein-coding mRNAs and lncRNAs can interact with each other competing for microRNA binding (Salmena et al. 2011). CeRNAs are thus lncRNAs that are particularly interesting considering the importance of the regulatory function of microRNAs.

Indeed, microRNAs, small evolutionarily conserved RNAs of 18-25 nucleotides, act as expression regulators of genes involved in fundamental processes, such as development, differentiation, proliferation, survival and death (Ambros 2004). Researchers in the field estimate that there are likely more than a thousand microRNAs in the human genome, and that these microRNAs may target up to one-third of all human genes (Croce 2009). A mature microRNA is loaded into the microRNA-induced silencing complex where it is believed to either repress mRNA translation or reduce mRNA stability following imperfect binding between the microRNA and MRE, typically within the 3' UTR of target genes (Garzon et al. 2010). MicroRNAs may function as tumor suppressors, oncogenes, or both. In many cases, these functions are disease or tissue-specific. Several observations implicated global deregulation of microRNAs in both solid and hematological malignancies (Croce 2009; Nana-Sinkam and Croce 2011).

In this study we show that the BRCA1-associated RING domain protein 1 (BARD1) gene expression may be regulated by a large number of microRNAs and by a presumed lncRNA competing for microRNA binding. BARD1 has tumor suppressor functions and is involved in a number of cellular processes including DNA repair, transcriptional regulation, chromatin remodeling, cell cycle checkpoint control, and mitosis (Jin et al. 1997; Hashizume et al. 2001; Westermark et al. 2003; Starita and Parvin 2003; Irminger-Finger and Jefford 2006; Joukov et al. 2006; Laufer et al. 2007; Murray et al. 2007; Ryser et al. 2009; Larsen et al. 2010; Li and Yu 2013). BARD1 has also been shown to be essential for the maintenance of genomic stability (Irminger-Finger et al. 1998; McCarthy et al. 2003; Li and Yu 2013). Several protein-coding mRNA isoforms of variable exon composition are expressed in human and murine cancers (Feki et al. 2005; Wu et al. 2006a; Li et al. 2007b; Lombardi et al. 2007; Sporn et al. 2011; Zhang et al. 2012a, 2012b). The full length (FL) BARD1 mRNA includes 11 exons (FIG. 1A) and encodes a protein comprising an N-terminal RING-finger domain, three ankyrin repeats (ANK), and two C-terminal BRCT domains. In cancer, the mRNA encoding tumor suppressor FL BARD1 is often down-regulated, while the expression of other splice isoforms is boosted. The overexpression of BARD1 isoforms that lack RING or RING and ANK was not only associated with breast, ovarian, endometrial, cervical, lung, and colon cancer (Wu et al. 2006a; Li et al. 2007b; Sporn et al. 2011; Zhang et al. 2012a, 2012b), but also correlated with advanced cancer stages of breast and ovarian cancer (Li et al. 2007b) and decreased patient survival time in lung cancer (Zhang et al. 2012a). Many studies suggest that the deficiency of FL BARD1 may have an oncogenic effect (Irminger-Finger et al. 1998; McCarthy et al. 2003; Tsuzuki et al. 2006; Capasso et al. 2009; Sabatier et al. 2010; Sporn et al. 2011) which would be consistent with the expression of spliced isoforms (Li et al. 2007a; Ryser et al. 2009; Ratajska et al. 2011; Bosse et al. 2012).

Importantly, SNPs in non-coding regions of or close to the BARD1 gene were clearly associated with neuroblastoma (Capasso et al. 2009; Nguyen et al. 2011; Latorre et al. 2012; Lee et al. 2013), and expression of isoforms was upregulated in the neuroblastoma-associated SNP genotype and correlated with disease progression and poor outcome (Bosse et al., 2012). In this study we provide evidence that a lncRNA expressed from an alternative intronic promoter of BARD1 may positively regulate BARD1 isoform expression.

BRIEF DESCRIPTION OF THE DRAWINGS

FIG. 1A shows the structures of two BARD1 mRNAs. FIG. 1B shows the schematic exon structure of protein coding full length (FL) BARD1 mRNA and splice isoforms. FIG. 1C shows RT-PCR to amplify BARD1 FL and other splice isoforms, using the primers as indicated on top. FIG. 1D shows RT-PCR to amplify BARD1 FL and other splice isoforms, using the primers as indicated on top.

FIG. 2C shows the predicted pairing of microRNAs with the region covering SNP rs7585356.

FIG. 2D shows the genomic conservation of the BARD1 3'UTR among vertebrates.

FIG. 3A shows an alignment of BARD' gene (top), BARD1 9'L RNA, and BARD1 9'S RNA structures. FIG. 3B shows DNA and deduced protein sequence of BARD1 9'S. FIG. 3C shows two BARD1 9' RNAs of different length, identified by 5'RACE PCR. FIG. 3D shows the expression of BARD1 9'S and BARD1 9'L investigated in four cancer cell lines. FIG. 3E schematically shows, on top, intron sequences in front of exon 9', with approximate position of the functional estrogen response elements (ERE). Below is shown an analysis of this DNA region for chromatin features that indicate the position of putative BARD1 9' promoter.

FIG. 4A shows RT-PCR of FL BARD1 (upper panel), BARD1 9'L (middle panel) and GAPDH as an internal control. FIG. 4B shows the localization of microRNA target sites in the BARD1 3'UTR present in BARD1 9'L. FIG. 4C shows the effect of miR-203 and miR-101 on BARD1 isoforms expression. FIG. 4D shows the quantification of RT-PCR signals of C.

FIG. 5A shows semi-quantitative RT-PCR for BARD1 9' isoforms using p9'_F2 forward and p11_R1 reverse primers.

FIG. 5B shows a histogram demonstrating the proportion of up-regulated, unchanged, and down-regulated BARD1 9'L expression in pairs of tumor/peri-tumor biopsies.

SUMMARY OF THE INVENTION

Figures 1A, 1B, 1C, 1D:
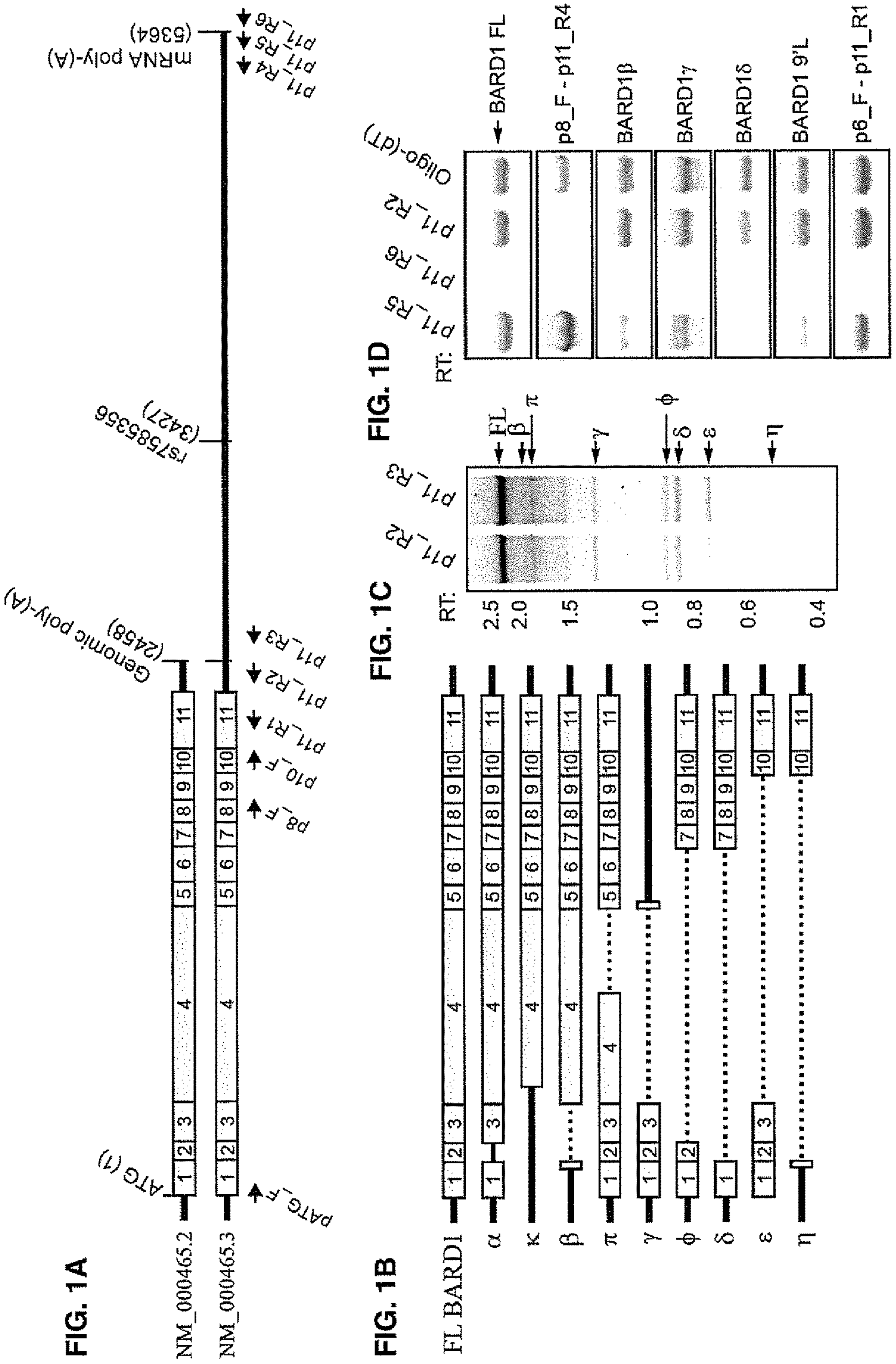
FIGS. 1A-1D show BARD1 mRNA and 3'UTR.

The inventions relates to a long non-coding BARD1 RNA molecule and to methods of using the same.

In an aspect, the inventions relates to the long non-coding BARD1 RNA molecule BARD1 9'L comprising or consisting of by Sequence 1.

In another aspect the invention relates to a RNA molecule according to claim 1 characterized by additions or deletions, optionally at the 5' or/and 3' end from 5 to 1000 nucleotides.

Furthermore an aspect is a siRNA specifically interfering with the expression or function of BARD1 9'L.

In particular preferred are siRNAs targeting the sequence unique for BARD1 9'L (Sequence 2) comprising or consisting of a sequence as depicted in Table 2.

The one or more siRNA molecules of the invention can be applied for use as a medicament. In particular one or more siRNA molecules of the invention is useful for use in preventing or treating cancer, preferably pancreatic, prostate, neuroblastoma, liver, lung, colorectal cancer, breast cancer or leukemia.

BARD1 9'L can be applied for use in screening compounds for their usefulness in cancer prevention or treatment.

Another aspect is a method of screening for compounds, optionally siRNA, useful in the prevention or treatment of cancer wherein i. the compounds are applied to cells expressing BARD1 9'L, ii. measuring with known techniques FL BARD1 and BARD1 isoforms wherein their level of expression is indicative of the usefulness of the compound in the prevention or treatment of cancer.

Yet another aspect is a method for the identification and/or quantification of BARD1 9'L in one or more cells, optionally wherein the cells are harvested under suitable conditions, the nucleic acid molecules of said cells are collected with a suitable technique, the collected nucleic acid molecules are subject to RT-PCR under suitable conditions wherein one or more primers hybridizing under suitable conditions with BARD1 9'L or cDNA produced on the BARD1 9'L RNA template, optionally of Table 2, are used, and BARD1 9'L is identified and/or quantified with known techniques.

A method for the prevention or treatment of cancer in a patient in need thereof comprising the steps of: i. identifying the expression of BARD1 9'L in a sample of said patient, optionally quantifying the level of expression, ii. administering an effective amount of one or more siRNAs as described herein to patients who express BARD1 9'L, preferably in a predefined amount or concentration.

The sample is preferably blood or a biopsy and the identification or/and quantification is preferably performed by RT-PCR or deep sequencing.

The invention will be useful preferably for the following aspects:

Therapeutic target: Novel BARD1 9' L sequence as a target for cancer treatment.

Therapeutic: BARD1 9'L sequence-specific siRNA set for direct inhibition of BARD1 9'L.

Diagnostic: primer set for RT-PCR detection/quantification of BARD1 9'L in patient samples.

The invention is based on the finding that non-coding RNA splice form encoded by the gene involved in oncogenesis (i.e. BARD1) can act as ceRNA and reduce the activity of micro-RNAs affecting BARD1, or BARD1 isoform expression. This will allow target treatment of certain forms of cancer.

The inventors found that the 3'UTR of BARD1 is significantly longer (~3500b) than previously reported (~120b). SNP rs7585356, located within the newly identified BARD1 3'UTR, is highly correlated with aggressive neuroblastoma and may affect specificity of several microRNAs targeting this region. This finding suggests that regulation of BARD1 and BARD1 isoform expression by microRNAs is critical for carcinogenesis, and furthermore, strengthens the importance of ceRNAs and BARD1 9'L in particular. The inventors found that the knock down of BARD1 9'L expression will reduce the expression of protein-coding oncogenic BARD1 isoforms in cancer cells and affect their proliferation.

Experimental data show for a number of cancers a correlation in expression of BARD1 9'L.

Experimentation can also show that down-regulation of BARD1 9'L through siRNA reduces cell proliferation.

The advantage of some aspects of the invention is inter alia that compared to the chemotherapy the proposed treatment will have less side effects and will be specific for the cancer cells where BARD1 9'L is abnormally unregulated. The use of siRNAs for BARD1 9'L inhibition will allow fast and specific inactivation of oncogenic BARD1 9'L and the isoforms depending on it.

In another aspect the invention relates to promoters which drive the transcription of BARD1 9'L.

We identified two putative promoters which may drive BARD1 9'L expression. The sequences and genomic location of these promoters are given in sequences 4 and 5 below.

The expression of BARD1 9'L may be suppressed on the level of transcription and thus diseases may be regulated, prevented or treated.

For targeting the promoter activity various approaches could be taken. The promoters could for example be modified through specifically engineered chromatin modifying enzymes.

The analysis of the chromatin modifications (DNA methylation, histone methylation, histone acetylation, transcription factors binding) of these sequences provides the information about the expression state of BARD1 9'L and as such may be used as a diagnostic tool. Accordingly, the invention in another aspect relates to a method for screening for compounds or molecules useful in modulating the expression of the BARD1 9'L promoters as depicted in sequences 4 and 5. Such methods include in vitro and in vivo assays wherein one or both of the promoter sequences is applied in a suitable setup, the compounds to be tested are applied under suitable conditions and a means for a read out of promoter activity is comprised in the setup. In this way compounds useful as drug for promoter regulation can be identified.

The compounds identified with such a method can in turn be used as medicament and in particular will be useful for the prevention of treatment of cancer.

Modulators of the BARD1 9'L promoter of the invention can be e.g. chromatin modifying enzymes or other enzymes or compounds modifying the promoter activity.

DETAILED DESCRIPTION OF PREFERRED EMBODIMENTS AND EXAMPLES

Materials and Methods

Construction of the Expression Vectors

BARD1 9'L cDNA was amplified using forward p9'_F1 (CCT GGG AAT CCC AAG GGT TC; SEQ ID NO:75) and reverse p11_R3 (CAT GAT AAA TCA AAA ACA TGC C; SEQ ID NO:71) primers and cloned into the Invitrogen pcDNA3.1(+) vector Cell Culture and Transfection Cells were cultured in D-MEM medium (Invitrogen) supplied with 10% FCS and penicillin/streptomycin and cultured at 37° C. in a humidified 5% CO2 incubator. The cells were transfected with plasmid DNA, miR-203 and miR-101 mimics (QIAGEN) individually, or co-transfected using Attractene® transfection reagent (QIAGEN) according to the manufacturer's guidelines. The expression of the genes of interest was assessed 48 h post-transfection. For transfection negative control, we used the empty Invitrogen pcDNA3.1(+) vector DNA or QIAGEN miScript Inhibitor Negative Control RNA.

Total RNA Extraction, Reverse Transcription and PCR

RT-PCR was performed for qualitative or semi-quantitative analysis of the expression of different BARD1 isoforms and for determination of their structure. RNA was isolated from cell culture pellets or frozen tissue samples using TRIzol® (Invitrogen) according to the manufacturer's instruction. Patients' materials were as described previously for colon cancer (Zhang et al. 2012b) and lung cancer (Zhang et al. 2012a).

Reverse transcription was performed using Promega M-MLV reverse transcriptase according to manufacturer's guidelines using oligo-(dT) or sequence specific primer. Two μl of reversed transcription reaction mixture were used for amplification of various fragments of BARD1 with Paq5000 polymerase (STRATAGEN) in 50 μl as described previously (Zhang et al. 2012a). Glyceraldehyde-3-phosphate dehydrogenase (GAPDH) was amplified as internal reference for RT-PV'CR reactions. For semi-quantitative PCR, the number of PCR cycles was adjusted to stop the reaction in the logarithmic amplification stage: 20 cycles for human GAPDH amplification and 25 cycles for the amplification of BARD1 isoforms. The PCR products were resolved on the agarose gels, imaged and quantified using Alpha-InnoTec software package (www dot alpha dot innotech dot ch). The quantification was based on three independent experiments.

The following primers were used for the RT and RT-PCR reactions:

| | | |
|---|---|---|
| | | (SEQ ID NO: 66) |
| pATG_F | ATG CCG GAT AAT CGG CAG CC | |
| | | (SEQ ID NO: 67) |
| p8_F | AGG GAT GGA CCT CTT GTA C | |
| | | (SEQ ID NO: 68) |
| p6_F | CTC CAG CAT AAG GCA TTG GT | |
| | | (SEQ ID NO: 69) |
| p11_R1 | CGA ACC CTC TCT GGG TGA TA | |
| | | (SEQ ID NO: 70) |
| p11_R2 | CAG CTG TCA AGA GGA AGC AAC | |
| | | (SEQ ID NO: 71) |
| p11_R3 | CAT GAT AAA TCA AAA ACA TGC C | |
| | | (SEQ ID NO: 72) |
| p11_R4 | AAG GGT TGA CTT ATA AAG AAA TAC | |
| | | (SEQ ID NO: 73) |
| p11_R5 | CAA CTT CTC AAT ATT TAT TTA TTC A | |
| | | (SEQ ID NO: 74) |
| p11_R6 | GCC AGG CAT AAG ACT ATT AGT TGA C | |
| | | (SEQ ID NO: 75) |
| p9'_F1 | CCT GGG AAT CCC AAG GGT TC | |
| | | (SEQ ID NO: 76) |
| p9'_F2 | CAA ATC ACT TAC AGT TTA ACA GAC G | |

BARD1 isoform specific forward primers were:

```
BARD1β Junct ex1-4
                                  (SEQ ID NO: 77)
CTG CTC GCG TTG ATT TGA AAG

BARD1γ Junct ex3-5
                                  (SEQ ID NO: 78)
CAA TGA GCT GTC AGG GCG AC

BARD1δ Junct ex1-7
                                  (SEQ ID NO: 79)
TGC TCG CGT TGT AAT ATA TTT G
```

5' RACE

The 5' RACE for BARD1 9' RNA was performed using 5' RACE System (Rapid Amplification of cDNA Ends) kit (Invitrogen, Catalog no. 18374-058) according to manufacturer's instructions. The following primers were used:

```
                                        (SEQ ID NO: 80)
5'RACE GSP1CTG TTA AAC TGT AAG TGA TTT GAC

                                        (SEQ ID NO: 81)
5'RACE GSP2CCA AGC TCA GCT AGC CAC ACA ACA G
```

Ethical Permission for the Patient Samples

Pathological diagnoses were made by experienced pathologists based on WHO criteria and staged according to American Joint Committee on Cancer classification. All patients were informed and compliance was obtained as well as approval of the local ethical committees.

Public Databases Analysis

To analyze publically available data (EST sequences, chromatin modification data, chromatin associated factors distribution) UCSC Genome Browser on Human (assembly GRCh37/hg19 and ENCODE/GENECODE version 19 data) was used. MiRNA target prediction and evaluation was performed using a Regulatory RNA Motifs and Elements Finder (RegRNA: http colon slash slash regrna dot mbc dot nctu dot edu dot tw slash html slash prediction dot html) and microRNA.org analysis tool.

The conservation of BARD1 3'UTR and intergenic region was analysed using 100 vertebrates Basewise Conservation by PhyloP (phyloP100wayAll) (Siepel et al. 2005; Pollard et al. 2009) with the help of UCSC Genome Browser (http colon slash slash genome dot ucsc dot edu).

Results

Identification of Long 3'UTR of BARD1 Containing a Large Number of Putative microRNA Target Sites We discovered that the reported 3'end of the known BARD1 mRNA sequence coincides with a genomic poly-A stretch at position 2457 relative to the start of translation of FL BARD1 in the BARD1 gene, suggesting that the reported end of the BARD1 3'UTR was likely an artifact of reversed transcription and poly(A) mapping (FIG. 1A). Thus, the 3'UTR of BARD1 may be longer then it was reported previously. This interpretation is supported by the recent reconstruction of the reference BARD1 gene sequence (GeneBank accession number NM_000465.3), which is partially based on the sequencing of an incomplete polyadenylated EST (GeneBank accession number BU753556) (FIG. 1A) that maps the position of the BARD1 polyadenylation site at nucleotide 5364 relative to the start of translation of FL BARD1.

The BARD1 gene comprises 11 exons spliced together to form the FL BARD1 mRNA (FIG. 1B). Several isoforms of BARD1 are generated by exon skipping. However, all mRNA isoforms seem to have the same 5' ends (FIG. 1B). Whether FL BARD1 and isoforms contain the same or different 3'UTR was an important question, and answers might provide a possible mechanism for the regulation of their respective expressions.

To verify whether FL BARD1 and BARD1 isoforms share the same extended 3'UTR beyond the reported 3'end at position 2457 relative to the start of translation of FL BARD1 (FIG. 1A), we performed reversed transcription using primers specific to the known BARD1 3'UTR (p11_R2), or a region downstream of position 2457 (p11_R3). Then we performed RT-PCR using a forward primer pATG_F annealing exon 1 of BARD1 and a reverse primer p11_R1 annealing to exon 11 of BARD1. We observed that all BARD1 isoforms were amplified equally well for both RT reactions (FIG. 1C). Thus, a 3'UTR longer than the reported 3'end is shared by all BARD1 splice isoforms.

To establish the length of the BARD1 3'UTR we performed RT-PCR using cDNA generated with RT primers p11_R5 and p11_R6 annealing correspondingly downstream and upstream of the poly-A site of BU753556 position (FIG. 1A) and compared this with the cDNA generated with p11_R2 and oligo dT primers (FIG. 1D). The amplification of p8_F-p11_R4 fragment was much less efficient for the oligo-dT generated cDNA then it was with the use of the cDNA generated with p11_R5 primer demonstrating that oligo-dT primer is not efficient for the generation of BARD1 cDNA with full sized 3'UTR.

FL BARD1 was amplified equally well in RT with the use of p11_R5, p11_R2 and oligo-dT suggesting that the majority of FL BARD1 mRNAs has a poly(A) tail at position 5364 relatively to the BARD1 ATG translation initiation codon. Importantly, the amplification of the fragments specific for BARD1 isoforms β, γ and δ was notably weaker for the p11_R5 cDNA then for p11_R2 and oligo-dT cDNAs. This suggests that a significant fraction of some oncogenic BARD1 isoforms with skipped exons possesses shorter 3'UTR using an alternative polyadenylation site.

The cDNA generated with p11_R6 primer did not generate a product with any of the primers used for PCR, indicating that the longest BARD1 mRNA has a poly(A) tail at position 5364 relatively to the start of translation of FL BARD1. This also rules out the possibility of RNA self-priming during the RT reaction, which may result in background amplification.

We conclude that the maximum length of the BARD1 3'UTR is 3030 nt. Considering that the median length of 3'UTRs of human mRNAs is about 500 nt (Mazumder et al. 2003), this might suggest an important regulatory role for the BARD1 3'UTR. To support this view we compared the 3'UTR of BARD1 between 100 vertebrate species. Interestingly, the BARD1 3'UTR includes a regions of high degree of conservation (FIG. 2B) suggesting a conserved regulatory role for this region, presumably linked to the microRNA functions.

Figure 2A:
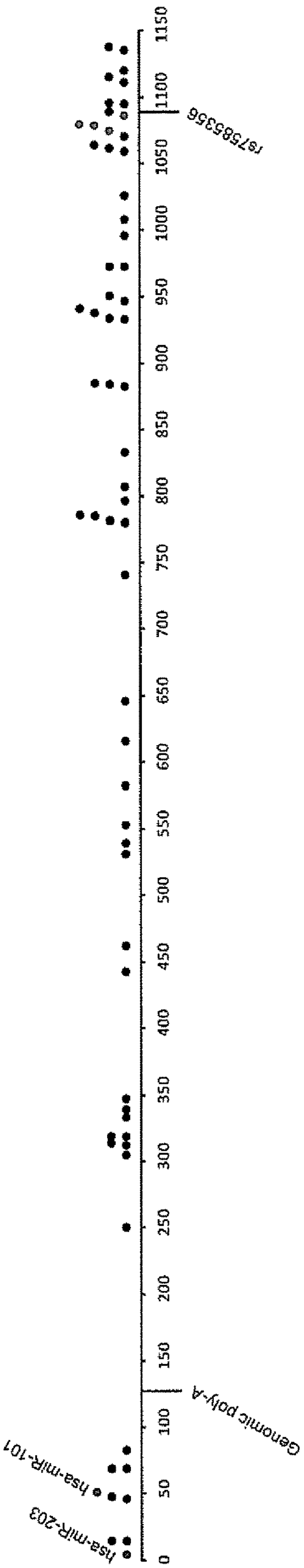
FIG. 2A shows the distribution of predicted high-score microRNAs on the BARD1 3'UTR sequence.

In addition, the BARD1 3'UTR contains a small nucleotide polymorphism (SNP) rs7585356, (FIG. 1A), which was identified in a genome wide association screen with aggressive neuroblastoma (Capasso et al. 2009). The effect of this SNP may now be explained by its localization within the 3'UTR of BARD1. We analyzed the region of the BARD1 3'UTR, from the BARD1 stop codon to the primer downstream of rs758535 (nucleotides 2335-2587, relative to the start of translation of FL BARD1) and identified a large number of high scoring and conserved putative microRNA target sites (FIG. 2A and Table 1). In particular, we found that several microRNAs could target the region around SNP rs7585356 (FIG. 2C). MiR-513c and miR-514b-5p only target the neuroblastoma-associated “A” (Capasso et al. 2009) but not the “C” genotype of the SNP rs7585356. The rs7585356 genotype may also affect the targeting of microRNAs miR-588 and miR-668. SNP rs7585356 seems to be a hotspot for microRNA binding and this may provide an explanation for the association of SNP rs7585356 with neuroblastoma. Further, we found that the genomic sequence flanking the SNP rs7585356 has significant degree of conservation between 10 mammalian species (FIG. 2D) compared to the inter-genic non-transcribed regions.

The BARD1 Gene Encodes a Non-Coding RNA with Alternative Transcription Start

Figures 3A, 3B, 3C, 3D, 3E:
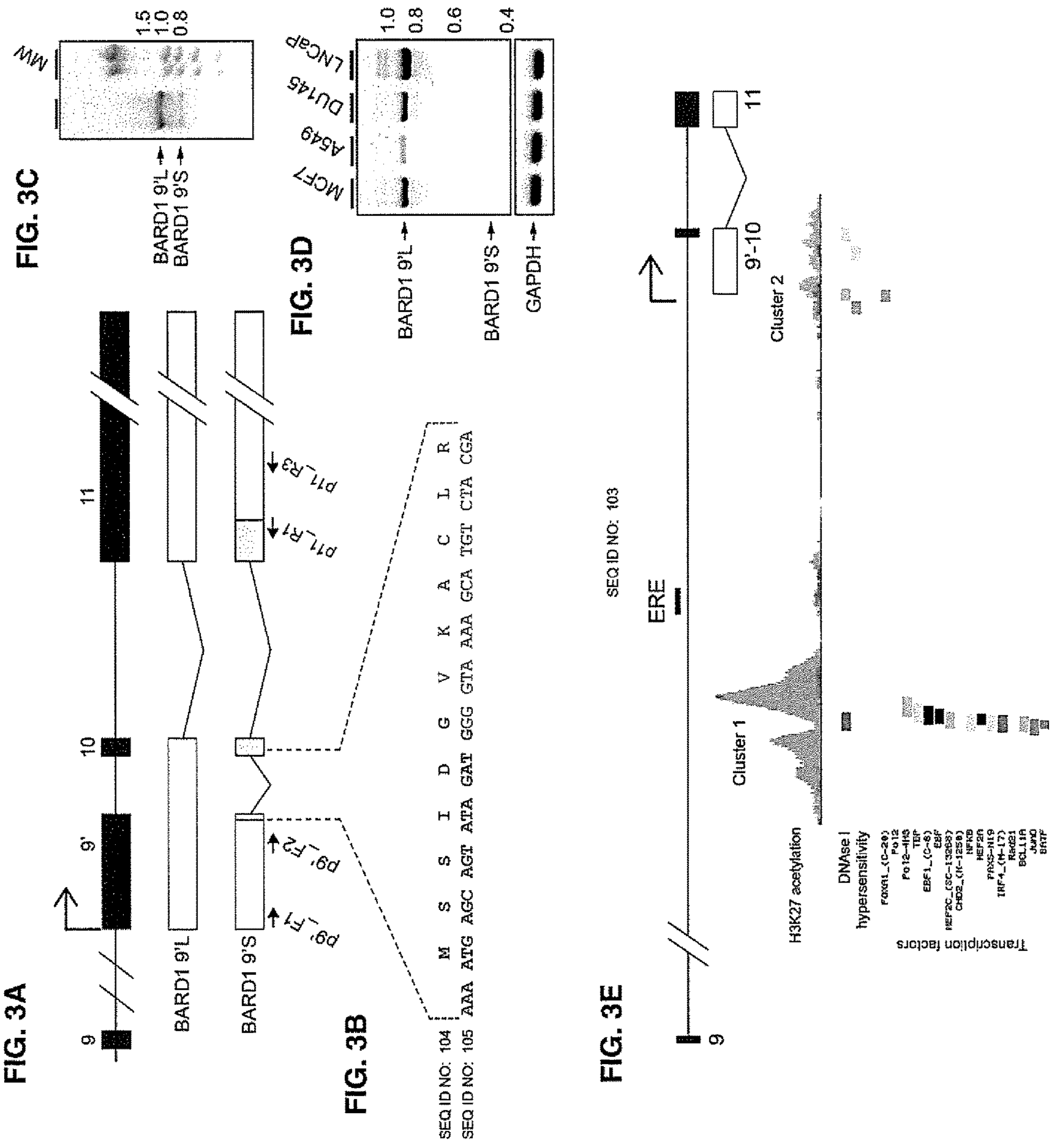
FIGS. 3A-3E show the characterization of the structure and expression of BARD1 9'S and 9'L isoforms.

We identified an incomplete spliced EST sequence (accession number AK310759) comprising exons 10 and 11 of BARD1, which expanded beyond the reported 3'end of BARD1 at position 2458 respective to the translation start codon of BARD1. This mRNA contained an additional exon, termed exon 9', located within intron 9 of BARD1 (FIG. 3A). This isoform, designated BARD1 9'S, has an ORF that starts within exon 9' and may encode a polypeptide of 148 amino acids, of which amino acids 1-6 are unique for BARD1 9'S, while amino acids 7-148 correspond to amino acids 636-777 of FL BARD1 (FIG. 3B).

To identify the transcription start site of BARD1 9'S, we performed 5'RACE on RNA from breast cancer derived cell line MCF7 with nested primers specific to exon 9'. We found that BARD1 9'S contained additional 212 bp at the 5'end reflecting the 9'S transcription start site (FIG. 3A). Thus, we conclude that the BARD1 9'S isoform has a transcription start in intron 9 of BARD1, which is different from the transcription start of all other BARD1 isoforms described. Importantly, none of the previously described BARD1 mRNAs encoding exon 1 comprises exon 9', excluding the possibility that the 5'end of BARD1 9'S could be an incomplete version of an isoform derived from splicing.

Furthermore, the RACE experiment revealed also another, longer mRNA product, with the same transcription start site as BARD1 9'S (FIG. 3C). Sequence analysis demonstrated that this isoform did not splice the intron between exon 9' and exon 10, but contained a longer exon 9' which was directly fused to exon 10 (FIG. 3A). We termed this isoform BARD1 9'L. Interestingly, in contrast to BARD1 9'S, which may encode a protein of 148 amino acids, BARD1 9'L appears to be a non-coding RNA as it contains no ORFs longer than 65 codons (Kapranov et al. 2007; Dinger et al. 2009).

We investigated the expression of BARD1 9'S and BARD1 9'L in four human cancer cell lines: MCF7 (breast cancer), A549 (lung cancer), and DL145 and LNCaP (prostate cancer) by RT-PCR (FIG. 3E). Interestingly, we observed the BARD1 9'S isoform signal only in the MCF7 cell line. However, the BARD1 9'L isoform was expressed in all cell lines tested and was much more abundant than BARD1 9'S.

FL BARD1 and other isoforms comprising exon 1, have transcription start sites that are separated from the BARD1 9'S and 9'L isoforms transcription start by 78 kb. Therefore, they must be transcribed from different promoters and have independent regulatory sequences. Using publically available databases we analysed the distribution of chromatin modifications, DNAse hypertensive sites, and binding sites for protein factors associated with the regulation of gene activity in the vicinity of the putative BARD1 9' isoforms promoter sequence (FIG. 3E). We found two clusters of an increased level of histone H3K27 acetylation, a marker of regulatory regions associated with transcriptionally active chromatin. Cluster 1 is located approximately 5 kb upstream of the BARD1 9' transcription start site, cluster 2 overlaps the BARD1 9' transcription start site. Both H3K27 acetylation clusters co-localise also with clusters of DNAse hypersensitive sites and a number of transcription factor binding sites (FIG. 3E).

Interestingly, cluster 1 is adjacent to the functional 288 bp estrogen receptor α (ERα) binding element (ERE) (Creekmore et al. 2007). It was shown that treatment of MCF-7 cells with estrogen increased expression of FL BARD1 and BARD1 isoform mRNA and protein levels (Creekmore et al. 2007; Dizin and Irminger-Finger 2010). This ERE is located 73 kb downstream of the FL BARD1 transcription start site and 4.5 kb upstream of the BARD1 9' transcription start site and next to the H3K27 acetylation cluster 1, which might suggest that ERα/estrogen-dependent upregulation of FL BARD1 and BARD1 isoform expression might be regulated indirectly via the BARD1 RNAs transcribed from the 9' transcription start site.

BARD1 9'L Competes for Down-Regulation of the Expression of BARD1 Isoforms by miR-203 and miR-101

Figures 4A, 4B, 4C, 4D:
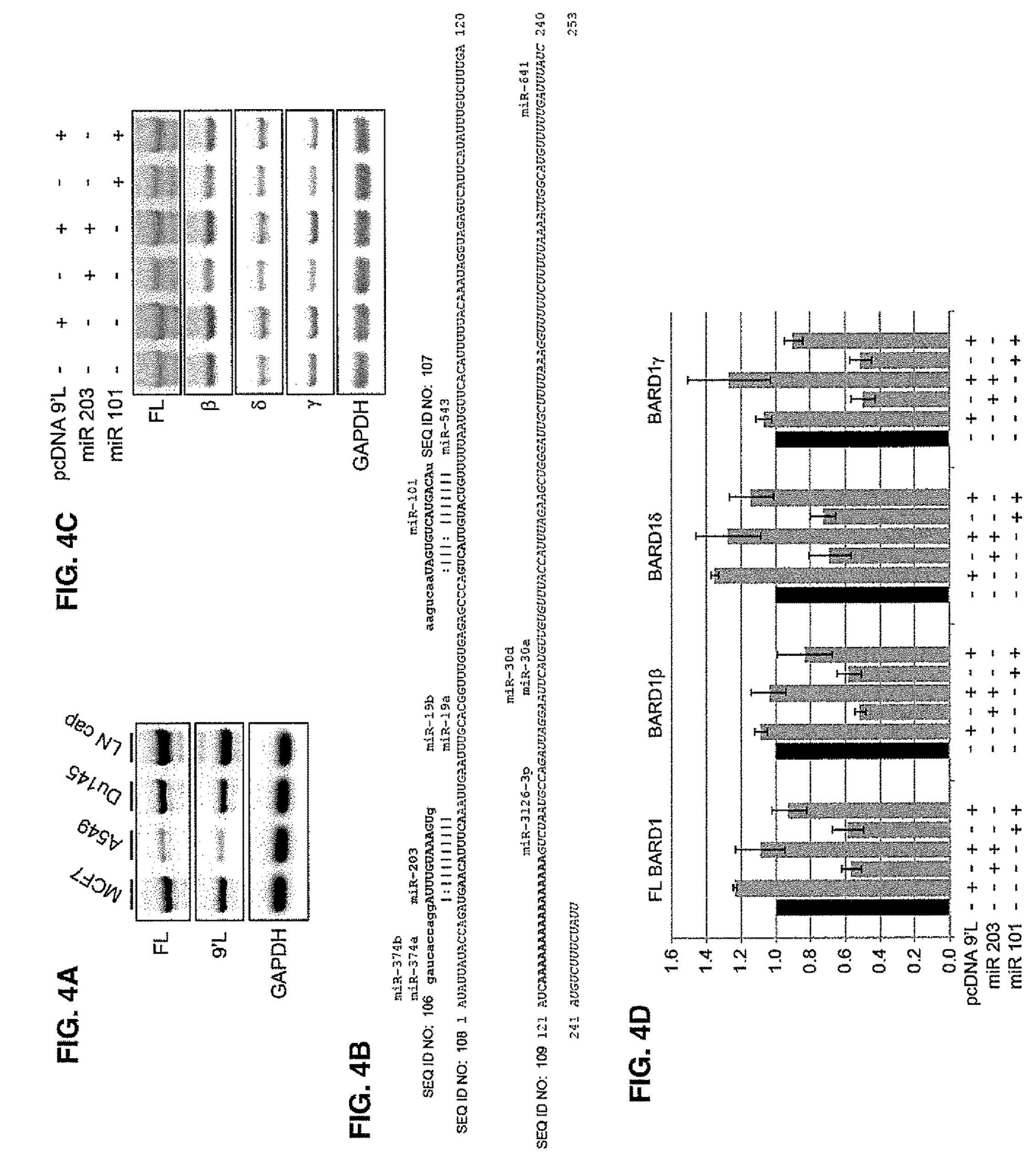
FIGS. 4A-4D show that BARD1 9'L counteracts the effect of miRNAs on BARD1 isoforms expression.

To investigate if BARD1 9'L RNA influences the expression of other BARD1 isoforms, we compared the expression levels of FL BARD1 and BARD1 9'L isoforms in the four human cancer cell lines MCF7, A549, DL145, and LNCaP and found that the expression levels of FL BARD1 and BARD1 9'L were correlated (FIG. 4B). This seemed reminiscent of the relationship between ceRNAs and the mRNAs which they compete for, e.g. PTEN-PTENP1 and KRAS1P-KRAS, a gene-oncogene relationship (Poliseno et al. 2010). We therefore hypothesized that BARD1 9'L may regulate FL BARD1 and BARD1 isoform expressions and functions.

To verify this hypothesis, we first cloned the BARD1 9'L isoform into the pcDNA expression vector using p9'_F1 and p11_R3 primers (FIG. 2A). The 3'end sequence of this clone (nucleotides 2335-2587, relative to the start of translation of FL BARD1) contains a number of high score and conserved putative microRNA target sites (FIG. 2A, 4A, Table 1), consistent with a role of 9'L as a competitor for microRNA binding.

To test the proposed relationship between microRNAs and BARD1 9'L and their effect on the expression of the BARD1 gene, we performed transfection assays, overexpressing BARD1 9'L and microRNAs. We choose the A549 cell line, which showed the lowest expression level of endogenous BARD1 9'L RNA of all the cell lines tested. We found that mimics of human miR-203 and miR-101 reduced the expression level of FL BARD1, BARD1β, BARD1δ, and BARD1γ mRNAs (FIG. 4C, D), suggesting a role of these microRNAs in reducing FL BARD1 and BARD1 isoform expression. At the same time, cells transfected with pcDNA vector expressing BARD1 9'L (pcDNA-9') showed increased levels of these mRNAs, suggesting that BARD1 9'L may protect BARD1 mRNAs from repression by endogenous microRNAs. Finally, when cells were co-transfected with miR-203 or miR-101 and pcDNA-9'L, the levels of BARD1 mRNAs were restored. These experiments demonstrate that BARD1 9'L may counteract the negative regulation of BARD1 mRNA expression by microRNAs in living cell.

The BARD1 9'L is over-expressed in cancer tissues Numerous studies showed that miR-203 has tumor suppressor functions in various cancer types (Gaur et al. 2007; Bueno et al. 2008; Feber et al. 2008) as its expression was abolished by chromosomal deletion or promoter CpG island hypermethylation in cancer cells (Bueno et al. 2008; Furuta et al. 2010). MiR-203 transcription was specifically repressed by the epithelial-mesenchymal translation (EMT) activator ZEB1, contributing to pancreatic and colorectal cancer cell invasive and metastatic behavior (Wellner et al. 2009). Accordingly, it has been demonstrated that miR-203 is significantly down-regulated in colorectal cancer cells (Chiang et al. 2011). The tumor suppressor role for miR-203 was also demonstrated in prostate cancer where it targets several genes controlling proliferation (Saini et al. 2010; Viticchiè et al. 2011). It was also shown that miR-203 is suppressed during EMT in the epithelial MCF-7 breast cancer cell line (Guttilla et al. 2011). Similarly, miR-101 has been shown to have tumor suppressor functions or is down-regulated in many types of cancer, including prostate cancer (Varambally et al. 2008; Hao et al. 2011), neuroblastoma (Buechner et al. 2011), liver (Leung-Kuen Au et al. 2012), and lung (Luo et al. 2011; Thu et al. 2011).

Figures 5A, 5B:
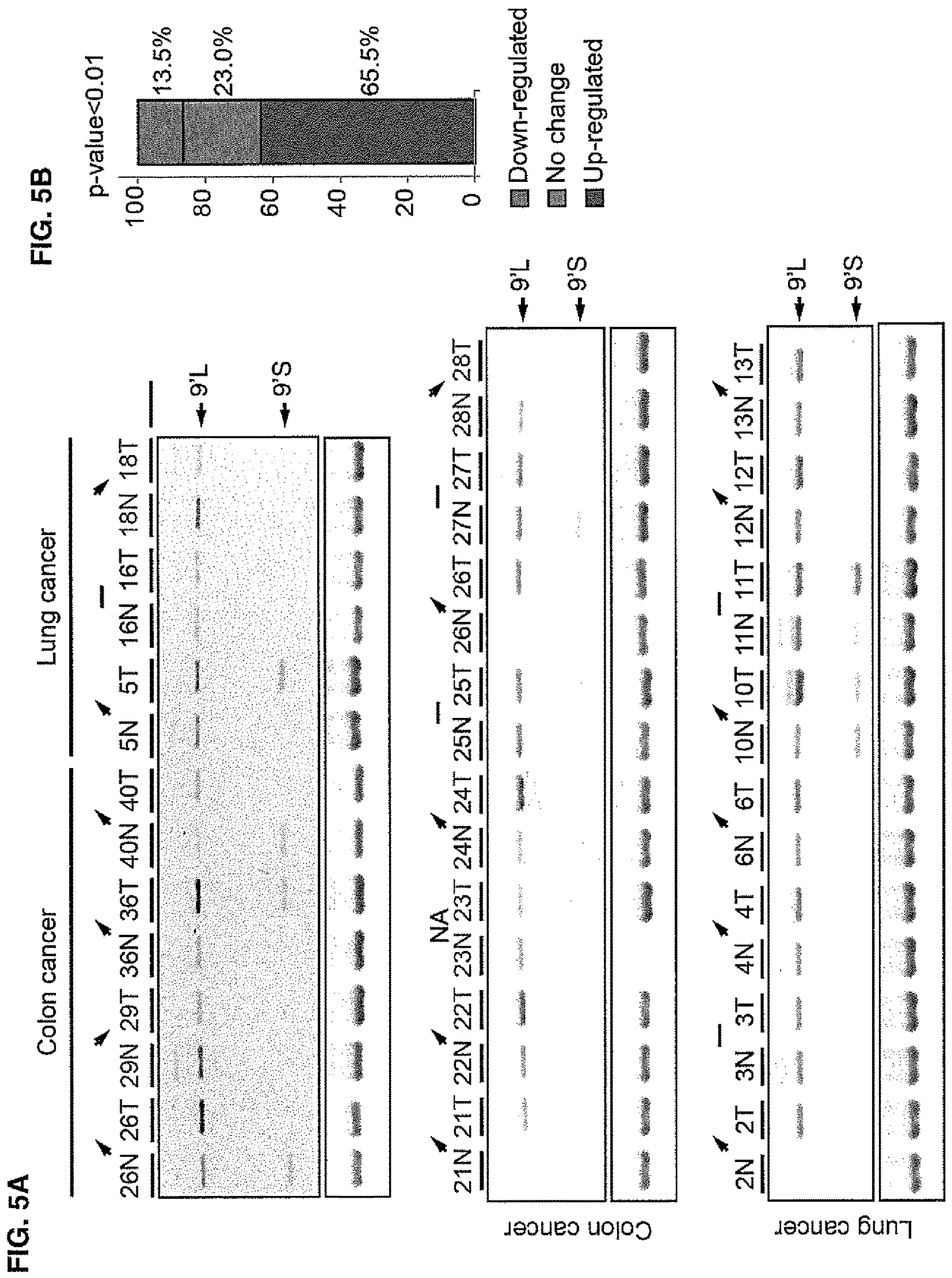
FIGS. 5A and 5B show BARD1 9'L expression in human cancers.

As overexpressed BARD1 isoforms are associated with cancer progression and can drive carcinogenesis, the expression of non-coding transcripts, such as BARD1 9'L, may protect them from down-regulation by tumor suppressor microRNAs, and this might contribute to carcinogenesis. We used a set of tumor and peri-tumor biopsy pairs from lung and colorectal cancer patients to investigate the level of expression of BARD1 9'L in cancer tissue. We found that BARD1 9'L expression was significantly higher in tumor tissues then in the paired peri-tumor samples (FIG. 5A, B). These findings support the hypothesis that BARD1 9'L may antagonizes the repressive effect of microRNAs on FL BARD1 and/or its isoforms.

It was observed that lncRNAs are highly abundant in cells, but their importance for the regulation of gene function is still argued (Wang et al. 2004; Dinger et al. 2009). There are not many examples of functional lncRNAs for which the mechanisms of action are known, but this number is growing. Here we show that the transcription of the BARD1 gene from an alternative intronic promoter produces a putative long non-coding RNA that shares 3'end sequences with protein coding BARD1 mRNAs and regulates their expression. Importantly, we found that the majority of FL BARD1 mRNAs has a very long 3'UTR with the poly(A) site at the position 5364 relatively to its start of translation, while BARD1 9'L, as well as some oncogenic BARD1 isoforms that lack internal exons form shorter 3'ends. This finding might add to the complexity of the regulation of expression of different products of the BARD1 gene, and suggests an important role for BARD1 9'L in carcinogenesis.

FL BARD1 is underrepresented or not present in cancer, while splice isoforms encoding truncated BARD1 protein variants are often over-expressed and associated with carcinogenesis. It has been shown that cancer-associated BARD1 isoforms antagonize the functions of FL-BARD1 as tumor suppressor and act as a driving force for carcinogenesis. Understanding the regulation of expression of FL BARD1 and its isoforms is therefore of utmost importance. The role for BARD1 9'L suggested here provides a mechanism for such regulation.

The BARD1 9'L consists of two exons, which are partially shared with the mRNAs transcribed from the BARD1 gene. The two-exon structure is the most common structure for lncRNAs (Derrien et al. 2012). BARD1 9'L is transcribed from an alternative independent promoter and, importantly, the profile of H3K27 acetylation in the putative BARD1 91 regulatory regions in intron 9 is more tissue specific than the bona fide BARD1 promoter upstream of exon 1. Modifications associated with active transcription from the intron 9 promoter of BARD1 were observed in only few cell types (beta-lymphocyte, blood vessel) in healthy individuals, while this alternative BARD1 promoter appears to be active in the majority of tissues reported in public databases. This implies an independent and specific regulation of the transcription of BARD1 9'S, and, more importantly, BARD1 9'L RNA.

We found that the 3'UTR of BARD1 is significantly longer than the median human 3'UTR, and we suggest that it has an important regulatory function. It may be involved in the regulation of mRNA transport and stability, or regulation by microRNAs. The last seems to be important for BARD1. There is indeed accumulating evidence linking the BARD1 3'UTR to microRNAs and cancer. We found that SNP rs7585356, which is associated with neuroblastoma, localized within and potentially affecting the target sequence of several microRNAs, and thus might be involved in the microRNA-dependent regulation of expression of BARD1 and its isoforms in neuroblastoma. It was also shown that miR-19a and miR-19b down-regulate the expression of the cancer-associated BARD1ω isoform in acute myeloid leukemia (Lepore et al. 2013). To verify the role for SNP rs7585356 and microRNAs presumably affected by this polymorphism, the effect of selected microRNAs on the expression of both variants of rs7585356 has to be tested in the reporter gene experiment.

It was discovered that microRNAs could induce de-adenylation of mRNAs. In general, de-adenylation leads to destabilization of mRNAs (Behm-Ansmant et al. 2006; Wu et al. 2006b; Wakiyama et al. 2007). We have identified a large number of microRNAs that could potentially bind the BARD1 3'UTR and regulate the stability of BARD1 mRNAs. Thus, regulation of BARD1 expression by microRNAs might be a general and important feature. The expression of BARD1 9'L, however, might be a tumor promoting feature. We demonstrate that two microRNAs that down-regulate BARD1 isoforms are competed for by BARD1 9'L, which counteracts their effect on BARD1 repression, supporting our hypothesis. To ultimately confirm BARD1 9'L function as a ceRNA, the direct action of microRNAs on its expression has to be demonstrated by mutating microRNA target sites and their effect has to be tested in the context of abolished Dicer activity. The specific knock-down of BARD1 9'L is also necessary to establish its effect on BARD1 expression in physiological conditions.

We found that BARD1 9'L is abnormally over-expressed in cancer. This overexpression could be induced by epigenetic modification of the BARD1 9'L promoter region. Other than the observed modifications (FIG. 3A), the BARD1 9' promoter might be modulated by hormones as it is in close vicinity of ERE which have been shown to be functional (Creekmore et al. 2007; Dizin and Irminger-Finger 2010). FL BARD1 and isoform expression is increased in response to hormone treatment in hormone-responsive cells derived from breast cancer. However, in hormone-non-responsive breast cancer cells BARD1 isoforms are constitutively up-regulated, suggesting regulatory elements that control hormone responsiveness are lost in these cells. BARD1 9'L could be the critical element in the switch from hormone-dependent expression to constitutive expression, through epigenetic modulation of its promoter. To clarify the mechanisms of BARD1 9'L promoter regulation, promoter assays using reporter genes have to be performed. The correlation of BARD1 9'L expression and the expression of protein-coding oncogenic BARD1 isoforms is particularly important for understanding its role in carcinogenesis and has to be addressed with the use of larger cohorts of patients.

Figure 6:
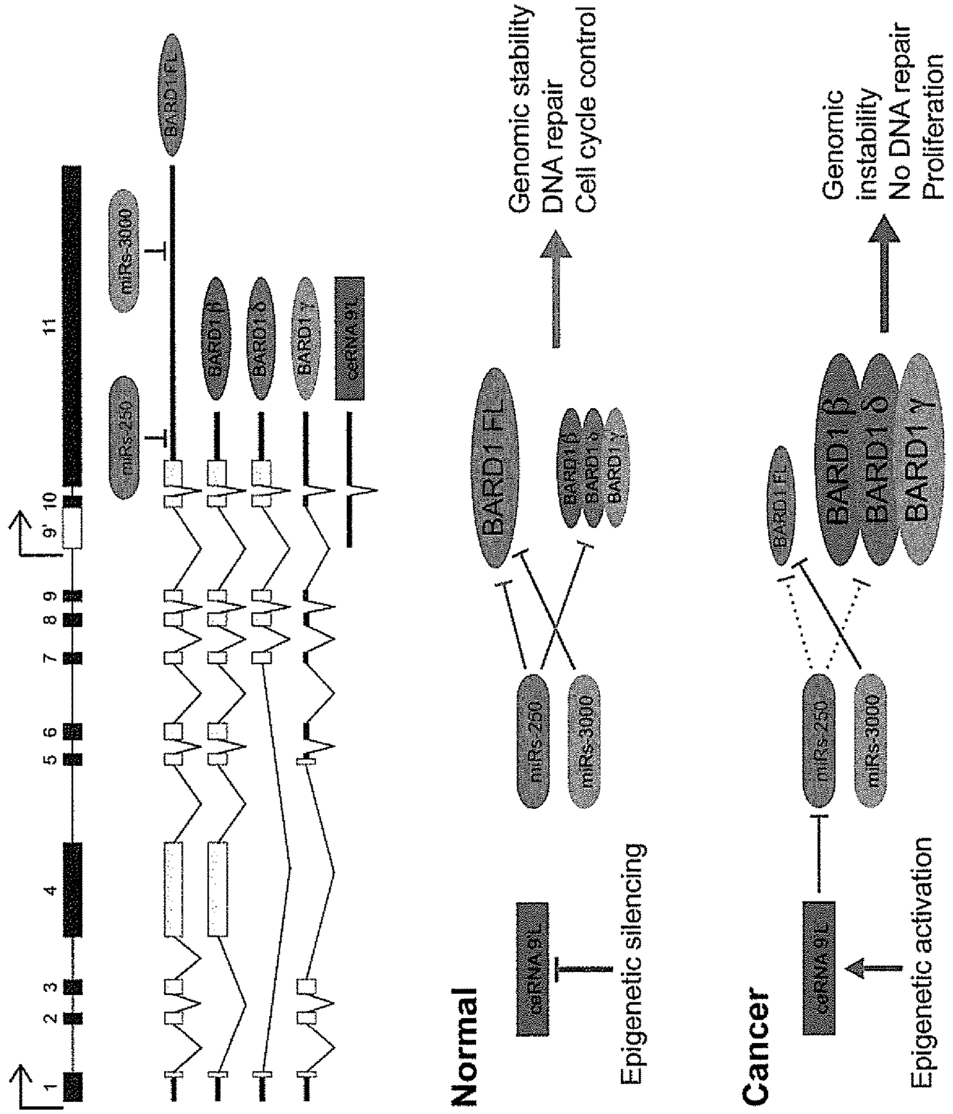
FIG. 6 shows the regulation of BARD1 and its isoforms by microRNAs and BARD1 9'L. On top, the intron-exon structure and 3'UTR regions of FL BARD1 and isoforms are aligned with positions of groups of microRNA binding sites indicated.

Based on our observations, we hypothesize that the promoter driving the expression of BARD1 9'L is silenced in normal tissues, while the bona fide BARD1 promoter is active and tumor suppressor FL BARD1 is predominantly produced (FIG. 6). In cancer cells changes in the epigenetic and hormone-dependent gene regulation accompanying carcinogenesis activate the expression of BARD1 9'L, which protects oncogenic BARD1 isoforms. Our data suggest that the initial 250 nucleotides of the BARD1 3'UTR are a minimal fragment of the BARD1 3'UTR equally shared by FL BARD1 and truncated BARD1 isoforms (FIG. 1 C, D). We demonstrated here that several of BARD1 mRNAs including FL BARD1 may be down-regulated by microRNAs seeding in the initial 250 nucleotides of the BARD1 3'UTR. Based on the above conclusions we denoted the minimal common BARD1 3'UTR region as miRNAs-250 (FIG. 6). At the same time, FL BARD1 having longer 3'UTR may still be down-regulated by microRNAs seeding in the region of the BARD1 3'UTR which is often missing in oncogenic BARD1 isoforms (miRNAs-3000). As a result, the ratio may be shifted in favor of oncogenic BARD1 isoforms thus driving carcinogenesis (FIG. 6). Considering that the BARD1 9' promoter appears to be inactive in healthy tissues, according to the available data, BARD1 9'L may represent a potential therapeutic target. Further experiments including isoform-specific 3' RACE and investigation of the effect of miRNAs-3000 on BARD1 mRNAs expression are necessary to define the BARD1 isoforms 3'UTRs and their role in the regulation of BARD1 expression.

Interestingly, BARD1 9'L shares 3'end sequences with protein-coding mRNAs. A large number of non-coding RNAs with similar structure were annotated recently, and systematic testing of the functionality of such RNAs expressed within the genes with important functions will be interesting for a better understanding of their role in gene expression regulation.

FIG. 1. BARD1 mRNAs and 3'UTR

FIG. 1A) The structures of two BARD1 mRNAs, BARD1 NM_000465.2 and BARD1 NM_000465.3 are shown. BARD1 NM_000465.2 mRNA represents the hitherto described BARD1 reference cDNA. BARD1 NM_000465.3 represents the longest BARD1 mRNA predicted on the base of analysis of available EST sequences. The positions of the NM_000465.2 poly(A) (genomic poly(A) stretch), the neuroblastoma-associated SNP rs7585356, and the NM_000465.3 poly(A) positions are indicated. Numbering is relatively to the translation start for FL BARD1. Arrows show the positions of the primers used for RT reactions and RT-PCR amplifications.

FIG. 1B) The schematic exon structure of protein coding full length (FL) BARD1 mRNA and splice isoforms is presented. Protein coding exons are presented as grey boxes or empty boxes for alternative ORFs, while lines represent non-coding sequences.

FIG. 1C) RT-PCR was performed using forward primet pATG_F and reverse p11_R1 or p11-R2 primers (FIG. 1B) to amplify BARD1 FL and other splice isoforms. All isoforms were amplified equally well from cDNA generated with primers within the reported BARD1 3'UTR (p11-R2) as with the primer downstream of the presumed polyadenylation signal at position 2457 (p11-R3).

FIG. 1D) The cDNA was generated with p11_R5 primer located upstream of the position of BARD1 NM_000465.3 mRNA poly(A), or p11_R6 primer located downstream of the position of BARD1 NM_000465.3 mRNA poly(A) site, or p11_R2 primer, upstream of the presumed polyadenylation at position 2457 relatively to the translation start codon of FL BARD1, or oligo-dT. RT-PCR was performed using the combinations of primers indicated at the right. Note that FL BARD1 is amplified equally well from RT reactions generated with p11_R5, p11_R2, or oligo-dT, while the amplification of p8_F-p11_R4 fragment is much less efficient for the oligo (dT) generated cDNA. Importantly, the amplification of the fragments specific for BARD1 isoforms 9'L, β, γ and δ is notably weaker for the p11_R5 cDNA then for p11_R2 and oligo-dT cDNAs. None of these fragments was amplified using the cDNA generated with p11_R6 primer indicating that the longest BARD1 mRNA ends with the poly(A) site at the position 5364 relatively to the start of translation of FL BARD1.

FIG. 2. The BARD1 3'UTR a Target for Numerous microRNAs

FIG. 2A) The distribution of predicted high-score microRNAs on the BARD1 3'UTR sequence (positions 1-1150 from the stop codon) is shown. MicroRNAs with confirmed effect on BARD1 mRNAs miR-203, miR-101, and miR-19a and 19b (Lepore et al., 2013) are shown in red, target sequences including SNP rs7585356, miR-513c, miR-514b-5p, miR-588 and miR-668, are shown in green.

Figure 2B:
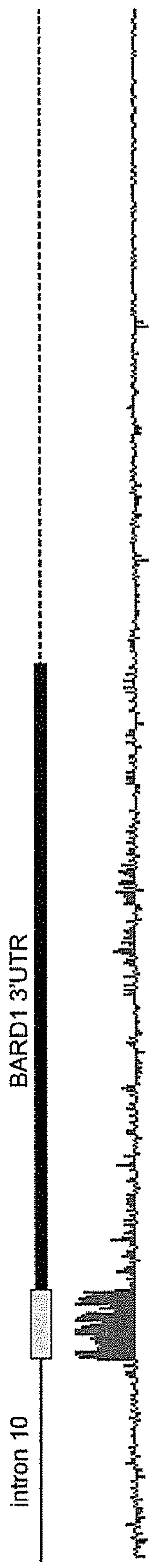
FIG. 2B shows genomic conservation of the BARD1 3'UTR among vertebrates.

FIG. 2B) Genomic conservation of the BARD1 3'UTR among vertebrates. The upper panel shows the fraction of the BARD1 intron 10 (black line) followed by exon 11 of the BARD1 gene (protein-coding part is represented by gray box, 3'UTR is shown as a black box). The inergenic region following BARD1 gene is shown as a dashed line. The lower panel demonstrates the degree of 100 vertebrates Basewise Conservation by PhyloP.

FIG. 2C) Predicted pairing of microRNAs with the region covering SNP rs7585356. Note that microRNAs hsa-miR-513c, hsa-miR-514b-5p, and hsa-miR-588 pair more efficiently to the SNP variant “U” associated with the genotype of healthy subjects, while hsa-miR-668 pairs more efficient to the SNP variant “C” associated with neuroblastoma.

FIG. 2D) The alignment of the genomic sequence covering SNP rs7585356 between different species is shown. Red bracket represents the sequence shown on the panel E in anti-sense direction. The polymorphism site is shown as dashed box.

FIG. 3. Characterization of Structure and Expression of BARD1 9'S and 9'L Isoforms FIG. 3A) The schemes of the BARD1 gene (top), BARD1 9'L RNA, and BARD1 9'S RNA structures are aligned. BARD1 9'L sequence does not have an ORF as it includes the intron between exon 9' and 10, 9'S does. The arrows indicate approximate positions of primers used for reversed transcription and PCR. White boxes represent non-translated sequence and grey boxes protein-coding sequences.

FIG. 3B) DNA and deduced protein sequence of BARD1 9'S is shown for the region of the junction between exon 9' (red) to exon 10 (black), beginning at first ATG and including in-frame splicing to exon 10.

FIG. 3C) 5'RACE PCR identifies two BARD1 9' RNAs of different length. BARD1 cDNA was synthesized using p11_R3 primer for RT reaction. BARD1 9'S and BARD1 9'L cDNAs were amplified with p9'_F1 and p11_R1 primers.

FIG. 3D) The expression of BARD1 9'S and BARD1 9'L was investigated in four cancer cell lines. RT-PCR was performed using forward p9'_F2 and reversed p11_R1 primers. BARD1 9'S RNA was only expressed in MCF7 cells and at low levels. BARD1 9'L was expressed in all four cell lines. GAPDH RT-PCR was used as a loading control (lower panel).

FIG. 3E) Schematic scheme of intron sequences in front of exon 9' is shown on top, with approximate position of the functional estrogen response elements (ERE). Arrow indicates the start of BARD1 9' transcription. Analysis of this DNA region for chromatin features that indicate the position of putative BARD1 9' promoter is shown below: Histograms indicate position of the histone H3K27 acetylation, an indicator of transcriptionally active regulatory sequences. The H3K27 acetylation is tissue specific and color coded as pink for beta-lymphocyte (Cluster 1) and blue for blood vessel (Cluster 2). The panel below represents the localization of DNAse I hypersensitive sites, and bottom panel shows the position of transcription factor (listed underneath) binding sites.

FIG. 4. BARD1 9'L Counteracts the Effect of miRNAs on BARD1 Isoforms Expression

FIG. 4A) Localization of microRNA target sites in the BARD1 3'UTR present in BARD1 9'L is shown. Positions 1-125 are BARD1 3'UTR sequence from the reference sequence NM_000465.2, and positions 126-253 correspond to newly identified BARD1 3'UTR sequence (shown in italic) and present in BARD1 9'L. Genomic poly-A stretch is shown in bold blue. The distribution of the most conserved and high-score microRNAs is shown. miR-203 and miR-101 sequences and their target sites are shown in bold red.

FIG. 4B) The expression level of BARD1 9'L correlates with the expression level of FL BARD1 in cancer cells. RT-PCR of FL BARD1 (upper panel), BARD1 9'L (middle panel) and GAPDH as an internal control are shown.

FIG. 4C) BARD1 9'L counteracts the effect of miR-203 and miR-101 on BARD1 isoforms expression. The A549 cell line was transfected with microRNA mimics and pcDNA vector expressing BARD1 9'L as indicated on the top with (+) or (−), scrambled control RNA or empty pcDNA vector. FL BARD1 expression was monitored by RT-PCR using pATG_F and p11_R1 primers, and expression of isoforms BARD1β, BARD1γ, and BARD1δ was determined by using isoforms-specific forward primers and p11_R1 as a reversed primer. Note, that miR-203 and miR-101 alone down-regulate the expression of all isoforms, while pcDNA-9'L alone up-regulates their expression and counteracts the effect of microRNAs when co-transfected. The representative images of RT-PCR electrophoresis are shown.

FIG. 4D) Quantification of RT-PCR signals of panel C. The intensity signals of BARD1 isoforms were normalized on the intensity of corresponding GAPDH signals (gray bars) and then normalized to the negative control signal values taken as 1.0 (black bars). Error bars show the standard deviation calculated for three independent experiments.

FIG. 5. BARD1 9'L Expression in Human Cancers.

FIG. 5A) Semi-quantitative RT-PCR for BARD1 9' isoforms using p9'_F2 forward and p11_R1 reverse primers. The expression of BARD1 9'L was monitored for 22 pairs tumor (T) and adjacent normal (N) tissues from biopsies. GAPDH was assessed as internal control.

FIG. 5B) The histogram demonstrates the proportion of up-regulated, unchanged, and down-regulated BARD1 9'L expression in pairs of tumor/peri-tumor biopsies. The number of cases with BARD1 9'L up-regulation in tumor tissues was statistically significantly ($p<0.01$) and higher then both down-regulation or unchanged according to the Fisher's exact test.

FIG. 6. Complex Regulation of BARD1 and its Isoforms by microRNAs and BARD1 9'L

Intron-exon structure and 3'UTR regions of FL BARD1 and isoforms are aligned (top) with positions of groups of microRNA binding sites indicated.

In normal cells the BARD1 9'L promoter is silenced. BARD1 9'L has a 3'end comprising positions 1-250 of the BARD1 3'UTR shown to be minimal common fragment for all tested BARD1 isoforms and responding on microRNA treatment. A combination of microRNAs targeting the BARD1 3'UTR, either positions 1-250 (miRs-250) or positions 251-3000) (miRs-3000), are expressed in a tissue-specific manner and effect repression of FL BARD1 as well as isoforms. FL BARD1 contains a long 3'UTR (positions 1-3000), but isoforms tend to have shorter 3'UTRs. Isoform with short 3'UTR BARD1β, BARD1γ, and BARD1δ are shown. Thus, in healthy tissues (normal) microRNAs maintain equilibrium of FL BARD1 and its isoforms in favor of FL BARD1 and maintenance of genomic instability, DNA repair, and cell cycle control functions of BARD1 are secured. In cancer cells, the BARD1 9'L promoter is active, BARD1 91 competes for binding microRNAs targeting the BARD1 3'UTR region 1-250, but not microRNAs targeting the 3'UTR region 251-3000, thus creating a disequilibrium in favor of BARD1 isoforms with a short 3'UTR. BARD1 isoforms antagonize FL BARD1 functions, which leads to genetic instability, loss of DNA repair and cell cycle control functions, and permits uncontrolled proliferation.

Table 1 contains a list of microRNAs potentially targeting the BARD1 3'UTR which are preferred embodiments of the invention

TABLE 1

List of miRNAs potentially targeting the BARD1 3'UTR

| Query | miRBase accession | Target position start/end | | Associated tissue, disease | Reference |
|---|---|---|---|---|---|
| hsa-miR-203 | MI0000283 | 4 | 25 | Myeloma, endometrial carcinoma, pancreatic adenocarcinoma | [5][3][14] |
| hsa-miR-19a | MIMAT0000074 | 14 | 39 | Neurons, AML | [11][1][12][3][4] |
| hsa-miR-19b | MI0000073 | 14 | 39 | Neurons, AML, fetal liver, cervix | [1][11][12][6][8][2][7][13][8][3][9][4] |
| hsa-miR-152 | MI0000462 | 46 | 67 | embryonic stem cells, cervix | [7][3][4][9][10] |
| hsa-miR-130a | MI0000448 | 48 | 66 | embryonic stem cells | [7][8][3][4] |
| hsa-miR-101 | MI0000103 | 51 | 68 | nasopharyngeal carcinoma, squamous cell carcinoma, neuroblastoma, liver cancer | [1][2][3][4] |
| hsa-miR-548c-5p | MIMAT0004806 | 69 | 90 | Colorectal cancer | [15][3] |
| hsa-miR-548h-5p | MIMAT0005928 | 69 | 90 | Colorectal cancer | [15][3] |
| hsa-miR-618 | MI0003632 | 83 | 103 | colorectal cancer | [15][3] |
| hsa-miR-1263 | MI0006398 | 250 | 270 | embryonic stem cells | [20] |
| hsa-miR-302a* | MIMAT0000683 | 305 | 331 | embryonic stem cells | [29][8][23][3] |
| hsa-miR-371a-5p | MIMAT0004687 | 312 | 331 | embryonic stem cells | [8][3] |
| hsa-miR-499a-5p | MIMAT0002870 | 314 | 336 | NA | [41][3] |
| hsa-miR-374a | MI0000782 | 319 | 342 | embryonic stem cells, cervix | [8][16][3][4] |
| hsa-miR-374b | MI0005566 | 319 | 342 | cervix | [17][3][4] |
| hsa-miR-3934 | MI0016590 | 333 | 354 | Psoriasis | [38][39] |
| hsa-miR-3692-5p | MIMAT0018121 | 339 | 361 | peripheral blood | [35] |
| hsa-miR-10b* | MIMAT0004556 | 347 | 368 | Colorectal cancer | [5][6][3][4] |
| hsa-miR-1271 | MI0003814 | 442 | 467 | embryonic stem cells; breast cancer | [17][20][21] |
| hsa-miR-514b-3p | MIMAT0015088 | 462 | 479 | Melanoma | [28][31][34][32] |
| hsa-miR-3941 | MI0016598 | 531 | 554 | NA | [38] |
| hsa-miR-4280 | MI0015889 | 539 | 562 | embryonic stem cells | [30] |
| hsa-miR-135a-3p | MIMAT0004595 | 553 | 573 | embryonic stem cells | [7][8][3] |
| hsa-miR-338-5p | MIMAT0004701 | 582 | 603 | Neurons; cervix | [22][23][3][4] |
| hsa-miR-377 | MI0000785 | 616 | 636 | NA | [36][16][3] |
| hsa-miR-624-5p | MIMAT0003293 | 646 | 668 | Colorectal cancer | [15][3] |

TABLE 1-continued

List of miRNAs potentially targeting the BARD1 3'UTR

| Query | miRBase accession | Target position start/end | | Associated tissue, disease | Reference |
|---|---|---|---|---|---|
| hsa-miR-3152 | MI0014179 | 741 | 762 | Melanoma | [17][31][28][32] |
| hsa-miR-151a-3p | MIMAT0000757 | 780 | 802 | Neurons; Cervical cancer | [22][23][13][3][4] |
| hsa-miR-378c | MI0015825 | 782 | 803 | embryonic stem cells | [30] |
| hsa-miR-422a | MI0001444 | 785 | 803 | HL-60 cell line | [40][3] |
| hsa-miR-378a | MI0000786 | 786 | 803 | pancreatic islet | [37][2][3] |
| hsa-miR-1269 | MI0006406 | 796 | 818 | embryonic stem cells | [20] |
| hsa-miR-3609 | MI0015999 | 807 | 831 | Cervical cancer | [34] |
| hsa-miR-298 | MI0005523 | 833 | 856 | NA | [3] |
| hsa-miR-3916 | MI0016422 | 883 | 909 | NA | [28] |
| hsa-miR-3202 | MIMAT0015089 | 884 | 906 | Melanoma | [31] |
| hsa-miR-3173 | MI0014204 | 885 | 908 | Melanoma | [31][32][33] |
| hsa-miR-205 | M10000285 | 933 | 955 | Cervical cancer; nasopharyngeal carcinomas | [5][3][4][26] |
| hsa-miR-2115 | MI0010634 | 934 | 956 | ovary | [27][28] |
| hsa-miR-346 | MI0000826 | 938 | 960 | Neurons | [22][23] |
| hsa-miR-1237 | MI0006327 | 941 | 962 | NA | [19] |
| hsa-miR-197 | MI0000239 | 947 | 968 | Cervical cancer | [24][3][4] |
| hsa-miR-34b | MI0000742 | 951 | 970 | embryonic stem cells | [29][3] |
| hsa-miR-1299 | MI0006359 | 973 | 998 | embryonic stem cells | [20] |
| hsa-miR-3148 | MI0014175 | 973 | 995 | Melanoma | [31] |
| hsa-miR-3149 | MI0014176 | 996 | 1018 | Melanoma | [31][28] |
| hsa-miR-1248 | MI0006383 | 1008 | 1034 | embryonic stem cells | [20] |
| hsa-miR-4290 | MI0015899 | 1026 | 1046 | embryonic stem cells | [30] |
| hsa-miR-1178 | MI0006271 | 1059 | 1085 | human sarcoma | [18] |
| hsa-miR-3680 | MI0016081 | 1062 | 1080 | peripheral blood | [35] |

TABLE 1-continued

List of miRNAs potentially targeting the BARD1 3'UTR

| Query | miRBase accession | Target position start/end | | Associated tissue, disease | Reference |
|---|---|---|---|---|---|
| hsa-miR-767-3p | MIMAT0003883 | 1064 | 1086 | NA | [17] |
| hsa-miR-1976 | MI0009986 | 1071 | 1089 | childhood acute lymphoblastic leukemia | [25] |
| hsa-miR-668 | MI0003761 | 1075 | 1105 | NA | [17][10] |
| hsa-miR-514b-5p | MIMAT0015087 | 1079 | 1101 | Melanoma; Cervix | [28][31][34][32] |
| hsa-miR-513c | MI0006649 | 1080 | 1101 | Cervix | [42][34] |
| hsa-miR-588 | MI0003597 | 1086 | 1107 | Colorectal cancer | [15] |
| hsa-miR-3126-3p | MIMAT0015377 | 1089 | 1110 | Breast | [30][28][31][32] |
| hsa-miR-222 | MI0000299 | 1095 | 1115 | embryonic stem cells; cervix; ovarian cancer | [5][8][2][3][4][27] |
| hsa-miR-662 | MI0003670 | 1096 | 1115 | Colorectal cancer | [15] |
| hsa-miR-2278 | MI0011285 | 1111 | 1132 | Teratoma | [21] |
| hsa-miR-520a-5p | MIMAT0002833 | 1115 | 1135 | NA | [3][41] |
| hsa-miR-3663-3p | MIMAT0018085 | 1120 | 1140 | NA | [38] |
| hsa-miR-362-5p | MIMAT0000705 | 1136 | 1162 | NA | [3][16][41] |
| hsa-miR-500a | MI0003184 | 1138 | 1163 | NA | [3][41] |

The list of the putative miRNA targeting BARD1 3'UTR at nucleotides 2335-3535, relative to the start of translation of FL BARD1. The miRNAs with the Minium Free Energy <−14.0 and score >140 according to the http colon slash slash regrna dot mbc dot nctu dot edu dot tw slash scan are listed. The miRNAs targeting SNP rs7585356 are highlighted in green.

REFERENCES

[1]. Mourelatos Z et al. (2002) PMID: 11914277. [2]. Kasashima K et al. (2004) PMID: 15325244. [3]. Landgraf P et al. (2007) PMID: 17604727. [4]. Lui W-O et al. (2007) PMID: 17616659. [5]. Lim L P et al. (2003) PMID: 12624257. [6]. Michael M Z et al. (2003) PMID: 14573789. [7]. Lagos-Quintana M et al. (2002) PMID: 12007417. [8]. Suh M-R et al. (2004) PMID: 15183728. [9]. Koh W et al. (2010) PMID: 20158877. [10]. Meunier J et al. (2013) PMID: 23034410. [11]. Lagos-Quintana M et al. (2001) PMID: 11679670. [12]. Dostie J et al. (2003) PMID: 12554860. [13]. Fu H et al. (2005) PMID: 15978578. [14]. Sonkoly E et al. (2007) PMID: 17622355. [15]. Cummins J M et al. (2006) PMTD: 16505370. [16]. Sewer A et al. (2005) PMID: 16274478. [17]. Berezikov E et al. (2006) PMID: 16954537. [18]. Subramanian S et al. (2008) PMID: 17922033. [19]. Berezikov E et al. (2007) PMID: 17964270. [20]. Morin R D et al. (2008) PMID: 18285502. [21]. Nygaard S et al. (2009) PMID: 19508715. [22]. Kim J et al. (2004) PMID: 14691248. [23]. Weber M J (2005) PMID: 15634332. [24]. Lagos-Quintana M et al. (2003) PMID: 12554859. [25]. Schotte D et al. (2009) PMID: 18923441. [26]. Zhu J Y et al. (2009) PMID: 19144710. [27]. Wyman S K et al. (2009) PMID: 19390579. [28]. Creighton C J et al. (2010) PMID: 20224791. [29]. Houbaviy H B et al. (2003) PMID: 12919684. [30]. Goff L A et al. (2009) PMID: 19784364. [31]. Stark M S et al. (2010) PMID: 20300190. [32]. Persson H et al. (2011) PMID: 21199797. [33]. Dannemann M et al. (2012) PMID: 22454130. [34]. Witten D et al. (2010) PMID: 20459774. [35]. Vaz C et al. (2010) PMID: 20459673. [36]. Altuvia Y et al. (2005) PMID: 15891114. [37]. Poy M N et al. (2004) PMID: 15538371. [38]. Liao J-Y et al. (2010) PMID: 20498841. [39]. Joyce C E et al. (2011) PMID: 21807764. [40]. Kasashima K et al. (2004) PMID: 15325244. [41]. Bentwich I et al. (2005) PMID: 15965474. [42]. Zhang R et al. (2007) PMID: 17416744.

TABLE 2 siRNAs specifically targeting BARD1 9'L (i.e. directed against the RNA sequence listed in Sequence 2 which is only present in BARD1 9'L but not in RNA encoding FL BARD1 or BARD1 isoforms)

| siRNA number | starting target position | ending target position | sense siRNA (5p-->3p) | antisense siRNA (5p-->3p) | SEQ ID NOs: |
|---|---|---|---|---|---|
| 1 | 14 | 32 | CAAGGGUUCCUU UCAUUUCTT | GAAAUGAAAGG AACCCUUGTT | 6, 7 |
| 2 | 15 | 33 | AAGGGUUCCUU UCAUUUCUTT | AGAAAUGAAAG GAACCCUUTT | 8, 9 |
| 3 | 16 | 34 | AGGGUUCCUUUC AUUUCUATT | UAGAAAUGAAA GGAACCCUTT | 10, 11 |
| 4 | 33 | 51 | UAGAGCCUAGCG AGACAAUTT | AUUGUCUCGCUA GGCUCUATT | 12, 13 |
| 5 | 34 | 52 | AGAGCCUAGCGA GACAAUUTT | AAUUGUCUCGCU AGGCUCUTT | 14, 15 |
| 6 | 111 | 129 | UGGAAUGACUC UAAACAGUTT | ACUGUUUAGAG UCAUUCCATT | 16, 17 |
| 7 | 112 | 130 | GGAAUGACUCU AAACAGUGTT | CACUGUUUAGA GUCAUUCCTT | 18, 19 |
| 8 | 164 | 182 | UAACCUGAAGCU GUGAACATT | UGUUCACAGCUU CAGGUUATT | 20, 21 |
| 9 | 228 | 246 | AGCCCAAUCAAA UCAUCUCTT | GAGAUGAUUUG AUUGGGCUTT | 22, 23 |
| 10 | 229 | 247 | GCCCAAUCAAAU CAUCUCUTT | AGAGAUGAUUU GAUUGGGCTT | 24, 25 |
| 11 | 230 | 248 | CCCAAUCAAAUC AUCUCUATT | UAGAGAUGAUU UGAUUGGGTT | 26, 27 |
| 12 | 269 | 287 | UACCUGUCACAU GCCAAACTT | GUUUGGCAUGU GACAGGUATT | 28, 29 |
| 13 | 270 | 288 | ACCUGUCACAUG CCAAACCTT | GGUUUGGCAUG UGACAGGUTT | 30, 31 |
| 14 | 275 | 293 | UCACAUGCCAAA CCUAUCCTT | GGAUAGGUUUG GCAUGUGATT | 32, 33 |
| 15 | 278 | 296 | CAUGCCAAACCU AUCCCAATT | UUGGGAUAGGU UUGGCAUGTT | 34, 35 |
| 16 | 353 | 371 | GCUUGGUGCUG UAGACUAATT | UUAGUCUACAGC ACCAAGCTT | 36, 37 |
| 17 | 354 | 372 | CUUGGUGCUGU AGACUAAATT | UUUAGUCUACA GCACCAAGTT | 38, 39 |
| 18 | 363 | 381 | GUAGACUAAAG CACAUUCCTT | GGAAUGUGCUU UAGUCUACTT | 40, 41 |
| 19 | 364 | 382 | UAGACUAAAGC ACAUUCCUTT | AGGAAUGUGCU UUAGUCUATT | 42, 43 |
| 20 | 376 | 394 | CAUUCCUUCAUG UCAAAUCTT | GAUUUGACAUG AAGGAAUGTT | 44, 45 |
| 21 | 377 | 395 | AUUCCUUCAUGU CAAAUCATT | UGAUUUGACAU GAAGGAAUTT | 46, 47 |
| 22 | 380 | 398 | CCUUCAUGUCAA AUCACUUTT | AAGUGAUUUGA CAUGAAGGTT | 48, 49 |
| 23 | 604 | 622 | GUUCAGUACUA ACUUAUGGTT | CCAUAAGUUAG UACUGAACTT | 50, 51 |
| 24 | 705 | 723 | GUAAGAUUUCU GUUUGCAUTT | AUGCAAACAGA AAUCUUACTT | 52, 53 |

TABLE 2-continued siRNAs specifically targeting BARD1 9'L (i.e. directed against the RNA sequence listed in Sequence 2 which is only present in BARD1 9'L but not in RNA encoding FL BARD1 or BARD1 isoforms)

| siRNA number | starting target position | ending target position | sense siRNA (5p-->3p) | antisense siRNA (5p-->3p) | SEQ ID NOs: |
|---|---|---|---|---|---|
| 25 | 760 | 778 | AAACCACUUAGG UAAAUUGTT | CAAUUUACCUAA GUGGUUUTT | 54, 55 |
| 26 | 761 | 779 | AACCACUUAGGU AAAUUGCTT | GCAAUUUACCUA AGUGGUUTT | 56, 57 |
| 27 | 801 | 819 | UAGUGCUCACUU GAUACUUTT | AAGUAUCAAGU GAGCACUATT | 58, 59 |
| 28 | 806 | 824 | CUCACUUGAUAC UUAGUUUTT | AAACUAAGUAU CAAGUGAGTT | 60, 61 |
| 29 | 807 | 825 | UCACUUGAUACU UAGUUUGTT | CAAACUAAGUA UCAAGUGATT | 62, 63 |
| 30 | 810 | 828 | CUUGAUACUUA GUUUGCUUTT | AAGCAAACUAA GUAUCAAGTT | 64, 65 |

REFERENCES

Ambros V. The functions of animal microRNAs. Nature. 2004 Sep. 16; 431(7006):350-5.

Behm-Ansmant I, Rehwinkel J, Doerks T, Stark A, Bork P, Izaurralde E. mRNA degradation by miRNAs and GW182 requires both CCR4:NOT deadenylase and DCP1:DCP2 decapping complexes. Genes & Development. 2006 Jul. 15; 20(14):1885-1898.

Birney E, Stamatoyannopoulos J A, Dutta A, Guigó R, Gingeras T R, Margulies E H, et al. Identification and analysis of functional elements in 1% of the human genome by the ENCODE pilot project. Nature. 2007 Jun. 14; 447(7146):799-816.

Bosse K R, Diskin S J, Cole K A, Wood A C, Schnepp R W, Norris G, et al. Common variation at BARD1 results in the expression of an oncogenic isoform that influences neuroblastoma susceptibility and oncogenicity. Cancer Res. 2012 Apr. 15; 72(8):2068-78.

Brown C J, Ballabio A, Rupert J L, Lafreniere R G, Grompe M, Tonlorenzi R, et al. A gene from the region of the human X inactivation centre is expressed exclusively from the inactive X chromosome. Nature. 1991 January 3; 349(6304):38-44.

Buechner J, Tømte E, Haug B H, Henriksen J R, Løkke C, Flægstad T, et al. Tumour-suppressor microRNAs let-7 and mir-101 target the proto-oncogene MYCN and inhibit cell proliferation in MYCN-amplified neuroblastoma. Br J Cancer. 2011 Jul. 12; 105(2):296-303.

Buena M J, Pérez de Castro I, Gómez de Cedrón M, Santos J, Calin G A, Cigudosa J C, et al. Genetic and epigenetic silencing of microRNA-203 enhances ABL1 and BCR-ABL1 oncogene expression. Cancer Cell. 2008 June; 13(6):496-506.

Capasso M, Devoto M, Hou C, Asgharzadeh S, Glessner J T, Attiyeh E F, et al. Common variations in BARD1 influence susceptibility to high-risk neuroblastoma. Nat Genet. 2009 June; 41(6):718-23.

Carninci P, Kasukawa T, Katayama S, Gough J, Frith M C, Maeda N, et al. The transcriptional landscape of the mammalian genome. Science. 2005 Sep. 2; 309(5740): 1559-63.

Chiang Y, Song Y, Wang Z, Chen Y, Yue Z, Xu H, et al. Aberrant expression of miR-203 and its clinical significance in gastric and colorectal cancers. J Gastrointest Surg. 2011 January; 15(1):63-70.

Creekmore A L, Ziegler Y S, Boney J L, Nardulli A M. Estrogen receptor alpha regulates expression of the breast cancer 1 associated ring domain 1 (BARD1) gene through intronic DNA sequence. Mol Cell Endocrinol. 2007 Mar. 15; 267(1-2):106-15.

Croce C M. Causes and consequences of microRNA dysregulation in cancer. Nat Rev Genet. 2009 October; 10(10):704-14.

Derrien T, Johnson R, Bussotti G, Tanzer A, Djebali S, Tilgner H, et al. The GENCODE v7 catalog of human long noncoding RNAs: analysis of their gene structure, evolution, and expression. Genome Res. 2012 September; 22(9):1775-89.

Dinger M E, Pang K C, Mercer T R, Crowe M L, Grimmond S M, Mattick J S. NRED: a database of long noncoding RNA expression. Nucl Acids Res. 2009 Jan. 1; 37(suppl 1):D122-D126.

Dizin E, Irminger-Finger I. Negative feedback loop of BRCA1-BARD1 ubiquitin ligase on estrogen receptor alpha stability and activity antagonized by cancer-associated isoform of BARD1. Int J Biochem Cell Biol. 2010 May; 42(5):693-700.

Feber A, Xi L, Luketich J D, Pennathur A, Landreneau R J, Wu M, et al. MicroRNA expression profiles of esophageal cancer. J Thorac Cardiovasc Surg. 2008 February; 135 (2):255-260; discussion 260.

Feki A, Jefford C E, Berardi P, Wu J-Y, Cartier L, Krause K-H, et al. BARD1 induces apoptosis by catalysing phosphorylation of p53 by DNA-damage response kinase. Oncogene. 2005 May 26; 24(23):3726-36.

Furuta M, Kozaki K, Tanaka S, Arii S, Imoto I, Inazawa J. miR-124 and miR-203 are epigenetically silenced tumor-suppressive microRNAs in hepatocellular carcinoma. Carcinogenesis. 2010 May; 31(5):766-76.

Garzon R, Marcucci G, Croce C M. Targeting microRNAs in cancer: rationale, strategies and challenges. Nat Rev Drug Discov. 2010 October; 9(10):775-89.

Gaur A, Jewell D A, Liang Y, Ridzon D, Moore J H, Chen C, et al. Characterization of microRNA expression levels and their biological correlates in human cancer cell lines. Cancer Res. 2007 Mar. 15; 67(6):2456-68.
Guttilla I K, Phoenix K N, Hong X, Tirnauer J S, Claffey K P, White B A. Prolonged mammosphere culture of MCF-7 cells induces an EMT and repression of the estrogen receptor by microRNAs. Breast Cancer Res Treat [Internet]. 2011 May 7 [cited 2011 Jun. 21]; Available from: http colon slash slash www dot ncbi dot nlm dot nih dot gov slash pubmed slash 21553120.
Hao Y, Gu X, Zhao Y, Greene S, Sha W, Smoot D T, et al. Enforced expression of miR-101 inhibits prostate cancer cell growth by modulating the COX-2 pathway in vivo. Cancer Prev Res (Phila). 2011 July; 4(7):1073-83.
Hashizume R, Fukuda M, Maeda I, Nishikawa H, Oyake D, Yabuki Y, et al. The RING heterodimer BRCA1-BARD1 is a ubiquitin ligase inactivated by a breast cancer-derived mutation. J Biol Chem. 2001 May 4; 276(18):14537-40.
He S, Liu S, Zhu H. The sequence, structure and evolutionary features of HOTAIR in mammals. BMC Evol Biol. 2011; 11:102.
Irminger-Finger I, Jefford C E. Is there more to BARD1 than BRCA1? Nat Rev Cancer. 2006 May; 6(5):382-91.
Irminger-Finger I, Soriano J V, Vaudan O, Montesano R, Sappino A P. In vitro repression of Brca1-associated RING domain gene, Bard1, induces phenotypic changes in mammary epithelial cells. J Cell Biol. 1998 Nov. 30; 143(5):1329-39.
Jin Y, Xu X L, Yang M C, Wei F, Ayi T C, Bowcock A M, et al. Cell cycle-dependent colocalization of BARD1 and BRCA1 proteins in discrete nuclear domains. Proc Natl Acad Sci USA. 1997 Oct. 28; 94(22):12075-80.
Joukov V, Groen A C, Prokhorova T, Gerson R, White E, Rodriguez A, et al. The BRCA1/BARD1 heterodimer modulates ran-dependent mitotic spindle assembly. Cell. 2006 Nov. 3; 127(3):539-52.
Kapranov P, Cheng J, Dike S, Nix D A, Duttagupta R, Willingham A T, et al. RNA Maps Reveal New RNA Classes and a Possible Function for Pervasive Transcription. Science. 2007 Jun. 8; 316(5830):1484-8.
Larsen D H, Poinsignon C, Gudjonsson T, Dinant C, Payne M R, Hari F J, et al. The chromatin-remodeling factor CHD4 coordinates signaling and repair after DNA damage. J Cell Biol. 2010 Sep. 6; 190(5):731-40.
Latorre V, Diskin S J, Diamond M A, Zhang H, Hakonarson H, Maris J M, et al. Replication of neuroblastoma SNP association at the BARD1 locus in African-Americans. Cancer Epidemiol Biomarkers Prev. 2012 April; 21(4): 658-63.
Laufer M, Nandula S V, Modi A P, Wang S, Jasin M, Murty V V V S, et al. Structural requirements for the BARD1 tumor suppressor in chromosomal stability and homology-directed DNA repair. J Biol Chem. 2007 Nov. 23; 282(47):34325-33.
Lee Y H, Kim J-H, Song G G. Genome-wide pathway analysis in neuroblastoma. Tumour Biol. 2013 Nov. 30;
Lepore I, Dell'Aversana C, Pilyugin M, Conte M, Nebbioso A, De Bellis F, et al. HDAC inhibitors repress BARD1 isoform expression in acute myeloid leukemia cells via activation of miR-19a and/or b. PLoS ONE. 2013 Dec. 11;
Leung-Kuen Au S, Chak-Lui Wong C, Man-Fong Lee J, Ngo-Yin Fan D, Hoching Tsang F, Oi-Lin Ng I, et al. Enhancer of zeste homolog 2 (EZH2) epigenetically silences multiple tumor suppressor miRNAs to promote liver cancer metastasis. Hepatology (Baltimore, Md.) [Internet]. 2012 Feb. 28 [cited 2012 Mar. 26]; Available from: http colon slash slash www dot ncbi dot nlm dot nih dot gov slash pubmed slash 22370893.
Li L, Cohen M, Wu J, Sow M H, Nikolic B, Bischof P, et al. Identification of BARD1 splice-isoforms involved in human trophoblast invasion. Int J Biochem Cell Biol. 2007 a; 39(9): 1659-72.
Li L, Ryser S, Dizin E, Pils D, Krainer M, Jefford C E, et al. Oncogenic BARD1 isoforms expressed in gynecological cancers. Cancer Res. 2007 b Dec. 15; 67(24):11876-85.
Li M, Yu X. Function of BRCA1 in the DNA Damage Response Is Mediated by ADP-Ribosylation. Cancer Cell. 2013 May 13; 23(5):693-704.
Lombardi G, Falaschi E, Di Cristofano C, Naccarato A G, Sensi E, Aretini P, et al. Identification of novel alternatively spliced BRCA1-associated RING domain (BARD1) messenger RNAs in human peripheral blood lymphocytes and in sporadic breast cancer tissues. Genes Chromosomes Cancer. 2007 September; 46(9):791-5.
Luo L, Zhang T, Liu H, Lv T, Yuan D, Yao Y, et al. MiR-101 and Mc1-1 in non-small-cell lung cancer: expression profile and clinical significance. Med Oncol [Internet]. 2011 Oct. 13 [cited 2012 Mar. 26]; Available from: http://www.ncbi.nlm.nih.gov/pubmed/21993632 http colon slash slash www dot ncbi dot nlm dot nih dot gov slash pubmed slash 21993632.
Matouk I J, Abbasi I, Hochberg A, Galun E, Dweik H, Akkawi M. Highly upregulated in liver cancer noncoding RNA is overexpressed in hepatic colorectal metastasis. Eur J Gastroenterol Hepatol. 2009 June; 21(6):688-92.
Mazumder B, Seshadri V, Fox P L. Translational control by the 3'-UTR: the ends specify the means. Trends in Biochemical Sciences. 2003 February; 28(2):91-8.
McCarthy E E, Celebi J T, Baer R, Ludwig T. Loss of Bard1, the heterodimeric partner of the Brca1 tumor suppressor, results in early embryonic lethality and chromosomal instability. Mol Cell Biol. 2003 July; 23(14):5056-63.
Murray M M, Mullan P B, Harkin D P. Role played by BRCA1 in transcriptional regulation in response to therapy. Biochem Soc Trans. 2007 November; 35(Pt 5):1342-6.
Nana-Sinkam S P, Croce C M. MicroRNAs as therapeutic targets in cancer. Translational Research. 2011 April; 157(4):216-25.
Nguyen L B, Diskin S J, Capasso M, Wang K, Diamond M A, Glessner J, et al. Phenotype restricted genome-wide association study using a gene-centric approach identifies three low-risk neuroblastoma susceptibility Loci. PLoS Genet. 2011 March; 7(3):e1002026.
Panzitt K, Tschernatsch M M O, Guelly C, Moustafa T, Stradner M, Strohmaier H M, et al. Characterization of HULC, a Novel Gene With Striking Up-Regulation in Hepatocellular Carcinoma, as Noncoding RNA. Gastroenterology. 2007 January; 132(1):330-42.
Poliseno L, Salmena L, Zhang J, Carver B, Haveman W J, Pandolfi P P. A coding-independent function of gene and pseudogene mRNAs regulates tumour biology. Nature. 2010 Jun. 24; 465(7301):1033-8.
Pollard K, Hubisz M, Siepel A. Detection of non-neutral substitution rates on mammalian phylogenies. Genome Res. 2009 Oct. 26; gr.097857.109.
Pouting C P, Oliver P L, Reik W. Evolution and Functions of Long Noncoding RNAs. Cell. 2009 Feb. 20; 136(4): 629-41.
Ratajska M, Antoszewska E, Piskorz A, Brozek I, Borg A, Kusmierek H, et al. Cancer predisposing BARD1 mutations in breast-ovarian cancer families. Breast Cancer Res Treat [Internet]. 2011 Feb. 23 [cited 2011 Aug. 2]; Available from: http colon slash slash www dot ncbi dot nlm dot nih dot gov slash pubmed slash 21344236.

Ryser S, Dizin E, Jefford C E, Delaval B, Gagos S, Christodoulidou A, et al. Distinct roles of BARD1 isoforms in mitosis: full-length BARD1 mediates Aurora B degradation, cancer-associated BARD1beta scaffolds Aurora B and BRCA2. Cancer Res. 2009 Feb. 1; 69(3):1125-34.

Sabatier R, Adélaïde J, Finetti P, Ferrari A, Huiart L, Sobol H, et al. BARD1 homozygous deletion, a possible alternative to BRCA1 mutation in basal breast cancer. Genes Chromosomes Cancer. 2010 December; 49(12):1143-51.

Saini S, Majid S, Yamamura S, Tabatabai Z L, Suh S O, Shahryari V, et al. Regulatory role of miR-203 in prostate cancer progression and metastasis. Clin Cancer Res [Internet]. 2010 Dec. 15 [cited 2011 Apr. 13]; Available from: http colon slash slash www dot ncbi dot nlm dot nih dot gov slash pubmed slash 21159887.

Salmena L, Poliseno L, Tay Y, Kats L, Pandolfi P P. A ceRNA Hypothesis: The Rosetta Stone of a Hidden RNA Language? Cell. 2011 Aug. 5; 146(3):353-8.

Siepel A, Bejerano G, Pedersen J S, Hinrichs A S, Hou M, Rosenbloom K, et al.

Evolutionarily conserved elements in vertebrate, insect, worm, and yeast genomes. Genome Res. 2005 Aug. 1; 15(8):1034-50.

Sporn J C, Hothorn T, Jung B H. BARD1 expression predicts outcome in colon cancer. Clin Cancer Res [Internet]. 2011 Jun. 21 [cited 2011 Jul. 29]; Available from: http colon slash slash www dot ncbi dot nlm dot nih dot gov slash pubmed slash 21693656.

Starita L M, Parvin J D. The multiple nuclear functions of BRCA1: transcription, ubiquitination and DNA repair. Current Opinion in Cell Biology. 2003 June; 15(3):345-50.

Thu K L, Chari R, Lockwood W W, Lam S, Lam W L. miR-101 DNA copy loss is a prominent subtype specific event in lung cancer. J Thorac Oncol. 2011 September; 6(9):1594-8.

Tsuzuki M, Wu W, Nishikawa H, Hayami R, Oyake D, Yabuki Y, et al. A truncated splice variant of human BARD1 that lacks the RING finger and ankyrin repeats. Cancer Letters. 2006 Feb. 20; 233(1):108-16.

Varambally S, Cao Q, Mani R-S, Shankar S, Wang X, Ateeq B, et al. Genomic loss of microRNA-101 leads to overexpression of histone methyltransferase EZH2 in cancer. Science. 2008 Dec. 12; 322(5908):1695-9.

Viticchié G, Lena A M, Latina A, Formosa A, Gregersen L H, Lund A H, et al. MiR-203 controls proliferation, migration and invasive potential of prostate cancer cell lines. Cell Cycle. 2011 Apr. 1; 10(7):1121-31.

Wakiyama M, Takimoto K, Ohara O, Yokoyama S. Let-7 microRNA-mediated mRNA deadenylation and translational repression in a mammalian cell-free system. Genes & Development. 2007; 21(15):1857-1862.

Wang J, Liu X, Wu H, Ni P, Gu Z, Qiao Y, et al. CREB up-regulates long non-coding RNA, HULC expression through interaction with microRNA-372 in liver cancer. Nucl Acids Res. 2010 Sep. 1; 38(16):5366-83.

Wang J, Zhang J, Zheng H, Li J, Liu D, Li H, et al. Mouse transcriptome: neutral evolution of "non-coding" complementary DNAs. Nature. 2004 Oct. 14; 431(7010):1 p following 757; discussion following 757.

Wapinski O, Chang H Y. Long noncoding RNAs and human disease. Trends Cell Biol. 2011 June; 21(6):354-61.

Wellner U, Schubert J, Burk U C, Schmalhofer O, Zhu F, Sonntag A, et al. The EMT-activator ZEB1 promotes tumorigenicity by repressing sternness-inhibiting microRNAs. Nat Cell Biol. 2009 December; 11(12):1487-95.

Westermark U K, Reyngold M, Olshen A B, Baer R, Jasin M, Moynahan M E. BARD1 Participates with BRCA1 in Homology-Directed Repair of Chromosome Breaks. Mol Cell Biol. 2003 November; 23(21):7926-36.

Wilusz J E, Sunwoo H, Spector D L. Long noncoding RNAs: functional surprises from the RNA world. Genes Dev. 2009 Jul. 1; 23(13):1494-504.

Wu J-Y, Vlastos A-T, Pelte M-F, Caligo M-A, Bianco A, Krause K-H, et al. Aberrant expression of BARD1 in breast and ovarian cancers with poor prognosis. Int J Cancer. 2006 a Mar. 1; 118(5):1215-26.

Wu L, Fan J, Belasco J G. MicroRNAs direct rapid deadenylation of mRNA. Proceedings of the National Academy of Sciences of the United States of America. 2006 b Mar. 14; 103(10:4034-4039.

Zhang Y-Q, Bianco A, Malkinson A M, Leoni V P, Frau G, De Rosa N, et al. BARD1: an independent predictor of survival in non-small cell lung cancer. Int J Cancer. 2012 a Jul. 1; 131(1):83-94.

Zhang Y-Q, Pilyugin M, Kuester D, Leoni V P, Li L, Casula G, et al. Expression of oncogenic BARD1 isoforms affects colon cancer progression and correlates with clinical outcome. British journal of cancer [Internet]. 2012 b Jul. 19 [cited 2012 Jul. 31]; Available from: http colon slash slash www dot ncbi dot nlm dot nih dot gov slash pubmed slash 22814582.

We claim:

1. A siRNA targeting a nucleotide sequence unique to long non-coding BARD1 9'L, wherein the BARD1 9'L unique nucleotide sequence consists of the sequence set forth in SEQ ID NO:2, wherein the BARD1 9'L unique nucleotide sequence is not present in an RNA encoding FL BARD1 or a BARD1 isoform, wherein the siRNA is complementary to a BARD1 9'L unique nucleotide sequence and reduces the expression of BARD1 9'L RNA.

2. A double stranded siRNA selected from the double stranded siRNAs set forth in Table 2 for siRNA 2-siRNA 30, the double stranded siRNA consisting of a sense sequence depicted in Table 2 for siRNA 2-siRNA 30 and its antisense sequence as depicted in Table 2 for siRNA 2-siRNA 30.

3. Two or more double stranded siRNAs selected from the double stranded siRNAs set forth in Table 2 for siRNA 2-siRNA 30, each double stranded siRNA consisting of a sense sequence as depicted in Table 2 for siRNA 2-siRNA 30 and its antisense sequence as depicted in Table 2 for siRNA 2-siRNA 30.

* * * * *